United States Patent
Lee et al.

(10) Patent No.: US 10,196,644 B2
(45) Date of Patent: Feb. 5, 2019

(54) METHOD FOR FINE-TUNING GENE EXPRESSION LEVELS USING SYNTHETIC REGULATORY SRNA

(71) Applicant: Korea Advanced Institute of Science and Technology, Daejeon (KR)

(72) Inventors: Sang Yup Lee, Daejeon (KR); Minho Roh, Daejeon (KR); Seung Min Yoo, Seoul (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/317,939

(22) PCT Filed: Jun. 11, 2014

(86) PCT No.: PCT/KR2014/005120
§ 371 (c)(1),
(2) Date: Dec. 9, 2016

(87) PCT Pub. No.: WO2015/190627
PCT Pub. Date: Dec. 17, 2015

(65) Prior Publication Data
US 2017/0130235 A1    May 11, 2017

(51) Int. Cl.
*C12N 15/67* (2006.01)
*C12N 15/113* (2010.01)

(52) U.S. Cl.
CPC ............ *C12N 15/67* (2013.01); *C12N 15/113* (2013.01); *C12N 2310/11* (2013.01); *C12N 2310/111* (2013.01); *C12N 2310/531* (2013.01)

(58) Field of Classification Search
None
See application file for complete search history.

(56) References Cited

U.S. PATENT DOCUMENTS

| | | |
|---|---|---|
| 2006/0057607 A1 | 3/2006 | Lenz et al. |
| 2010/0311137 A1 | 12/2010 | Brown et al. |
| 2014/0377752 A1* | 12/2014 | Lee .................. C12N 15/63 435/6.11 |

FOREIGN PATENT DOCUMENTS

| | | |
|---|---|---|
| KR | 10-2012-0140185 A | 12/2012 |
| KR | 10-2013-0082474 A | 7/2013 |

OTHER PUBLICATIONS

Sequence Alignment of SEQ ID No. 91 with SEQ ID No. 139. Search conducted on Sep. 22, 2017, 1 page.*
Datsenko, K., et al., "One-step Inactivation of Chromosomal Genes in *Escherichia coli* K-12 Using PCR Products", Proc. Natl. Acad. Sci. USA (PNAS), Jun. 6, 2000, pp. 6640-6645, vol. 97, No. 12.
Na, D., et al., "Metabolic Engineering of *Escherichia coli* Using Synthetic Small Regulatory RNAs", "Nature Biotechnology", Jan. 20, 2013, pp. 170-174, vol. 31, No. 2.
Na, D., et al., "Supplementary Information: Metabolic Engineering of *Escherichia coli* Using Synthetic Small Regulatory RNAs", "Nature Biotechnology", Jan. 20, 2013, pp. doi: 10.1038/nbt.2461.
Neumann, E., et al., "Gene Transfer into Mouse Lyoma Cells by Electroporation in High Electric Fields", "The EMBO Journal", Jun. 30, 1982, pp. 841-845, vol. 1, No. 7.
So, L.Y., et al., "pZMO7-Derived Shuttle Vectors for Heterologous Protein Expression and Proteomic Applications in the Ethanol-producing Bacterium *Zymomonas mobilis*", "BMC Microbiology", Mar. 15, 2014, pp. 1-16, vol. 14, No. 68.
Yoo, S.M., et al., "Design and Use of Synthetic Regulatory Small RNAs to Control Gene Expression in *Escherichia coli*", "Nature Protocols", Aug. 8, 2013, pp. 1694-1707, vol. 8, No. 9.

* cited by examiner

*Primary Examiner* — Channing S Mahatan
(74) *Attorney, Agent, or Firm* — Hultquist, PLLC; Steven J. Hultquist

(57) ABSTRACT

The present invention relates to a method for fine-tuning gene expression levels using a synthetic regulatory sRNA in a prokaryotic cell. The present invention can simultaneously, easily, and quickly apply various target gene combinations to various strains without gene deletion through the synthetic regulatory sRNA for regulating gene expression and is therefore very suitable for measuring the metabolizability of each strain and selecting an optimum strain. In addition, the method has the advantages of easily and quickly selecting a target gene for the inhibition of gene expression and expressing the gene thus selected to a desired degree and thus can be used in producing recombinant strains for the efficient production of various metabolites and establishing a method for the efficient production and is therefore very useful.

11 Claims, 11 Drawing Sheets
(11 of 11 Drawing Sheet(s) Filed in Color)
Specification includes a Sequence Listing.

SgrS-S

```
        U A
      U   A C
          A C
        A A C U
      A A U G C
    A A U G C U
    A U G C A C
    U G C U C G
    G C A U C G
5'-NNNNNNNNNNNNNNUAUG CCG UUUUUUUU-3'    SEQ ID NO: 92
```

1. Base pairing region
2. Hfq binding site
3. Rho-independent terminator

FIG. 2

METHOD FOR FINE-TUNING GENE EXPRESSION LEVELS USING SYNTHETIC REGULATORY SRNA

CROSS-REFERENCE TO RELATED APPLICATIONS

This application is a U.S. national phase under the provisions of 35 U.S.C. § 371 of International Patent Application No. PCT/KR14/05120 filed Jun. 11, 2014. The disclosure of such international patent application is hereby incorporated herein by reference in its entirety, for all purposes.

TECHNICAL FIELD

The present invention relates to a method for fine-tuning gene expression levels using synthetic regulatory sRNA in a prokaryotic cell and, and more specifically, to a synthetic regulatory sRNA capable of fine-tuning an expression of a target gene by regulating an expression level of sRNA or a binding affinity between the sRNA and Hfq so as to fine-tune the expression of the target gene.

BACKGROUND ART

Concerns about environmental problems and limited resource depletion have increased rapidly on a world-wide basis in recent years. Accordingly, there is an increasing interest in constructing an environmentally-friendly and reproducible organism-based production system as an alternative to these concerns. The system is capable of being constructed by regulating a metabolic pathway in an organism to optimize metabolic flow for production of desired metabolites, wherein various molecular biology techniques are required in this process. To regulate the metabolic pathway, there are two major techniques including one technology of increasing an enzyme expression required for a biosynthesis process to enhance metabolism flow required for the production of metabolites, and the other technology of blocking the metabolic flow used for cell growth and other metabolite productions and of deleting genes for utilization as target metabolite production. The currently widely used gene knock-out method is to substitute a gene to be deleted with any sequences having homologous sequences through recombinase, thereby losing function thereof (Datsenko et al, *PNAS*, 97(12): 6640-6645, 2000). However, this gene knock-out method has various problems.

First of all, the gene knock-out method requires several weeks—several months, and the gene expression is able to be regulated only by on-off, and gene deletion needs to be repeated for each strain to be applied to several strains. Therefore, it is the most time-consuming process in metabolic engineering studies in which a number of cases have to be confirmed experimentally. A method of inducing mutations in a promoter of a gene present on chromosome to weaken the activity or a method of substituting with various promoters that are capable of regulating gene expression instead of the existing promoters are used as a method for regulating and inhibiting a gene expression level. However, these methods are also performed through the same or similar processes as the gene knock-out method, and thus, they have limitation of the gene knock-out method through chromosomal recombination, and further, unlike the gene knock-out method, it is difficult to predict results until an expression level resulted from the mutant promoter is directly identified. Consequently, these methods may require more effort and time than simple gene knock-out method.

In order to overcome the limitations of this conventional gene inhibition method, a short-length customized synthetic sRNA technique has been developed (Na, D et al., *Nat. Biotechnol.*, 31(2), 170-174, 2013; Yoo, S M et al. *Nat. Protoc.*, 8(9), 1694-1707, 2013), which have advantages in that it is possible to easily reduce an expression of a target gene by using a plasmid without modifying chromosomal sequence of a target strain, and to easily apply the same gene expression inhibition to various strains in a multiple simultaneous manner. Moreover, this technique is quick and simple in view of construction, storage, and application.

An sRNA consists of Hfq binding sequence and a base pairing region (hereinafter, referred to as BPR) for complementary binding to the mRNA of the target gene. In order to regulate expression of the target gene, in the conventional technique, the binding free energy of the BPR part is calculated to control a base sequence length and mutation. This is advantageous because the BPR part is capable of being designed based on the base sequence information of the target gene and synthetic sRNA is capable of being easily designed and constructed through general gene recombination method. However, in order to fine-tune gene expression to a desired level, the BPR part of the sRNA needs to be redesigned for each target gene and the sRNA needs to be redesigned based on the redesigned BPR part. Further, the strategy using the binding free energy has a limitation in that it is difficult to accurately predict changes in sRNA activity. The binding free energy is calculated based on the sequence of sRNA and mRNA. In an actual binding of sRNA and mRNA, a prediction accuracy may be lowered because Hfq protein helps the binding of sRNA and mRNA. Further, when structural changes occur in the binding sequence due to a secondary structure of sRNA and mRNA, it is not possible to predict the degree of expression inhibitory activity. To overcome these problems, a general-purpose system capable of regulating the gene expression to a desired level regardless of the type of target gene or the sequence of BPR should be developed.

Therefore, the present inventors made an effort to construct the general-purpose gene expression regulatory system that meets the above conditions, and as a result, attempted mutation of other elements while fixing the BPR, and consequently, the general-purpose gene expression regulatory system was constructed by introducing promoters having various strength activities and applying a mutation to a Hfq binding site in the sRNA scaffold. It was confirmed that the expression of the target gene could be regulated by introducing various constitutive promoters to regulate the expression level of sRNA, and when an inducible promoter was introduced, it was confirmed that the expression of the target gene could be fine-tuned by introducing a mutation into the Hfq binding site of the sRNA scaffold, thereby completing the present invention.

DISCLOSURE

Summary of Invention

An object of the present invention is to provide a method for fine-tuning gene expression levels using customized synthetic sRNA capable of fine-tuning an mRNA expression of a target gene while simultaneously overcoming limitations of conventional methods for inhibiting gene expression.

DESCRIPTION OF DRAWINGS

The patent or application file contains at least one drawing executed in color. Copies of this patent or patent application publication with color drawing(s) will be provided by the Office upon request and payment of the necessary fee.

FIG. 2 shows a partial structure of the SgrS which is the sRNA, and shows a potential target to induce mutation. The 'UUUUUUUU' sequence at the 3' end of this sequence (SEQ ID NO: 92) is also a transcription terminator and Hfq binding site.

BEST MODE

Figure 1:
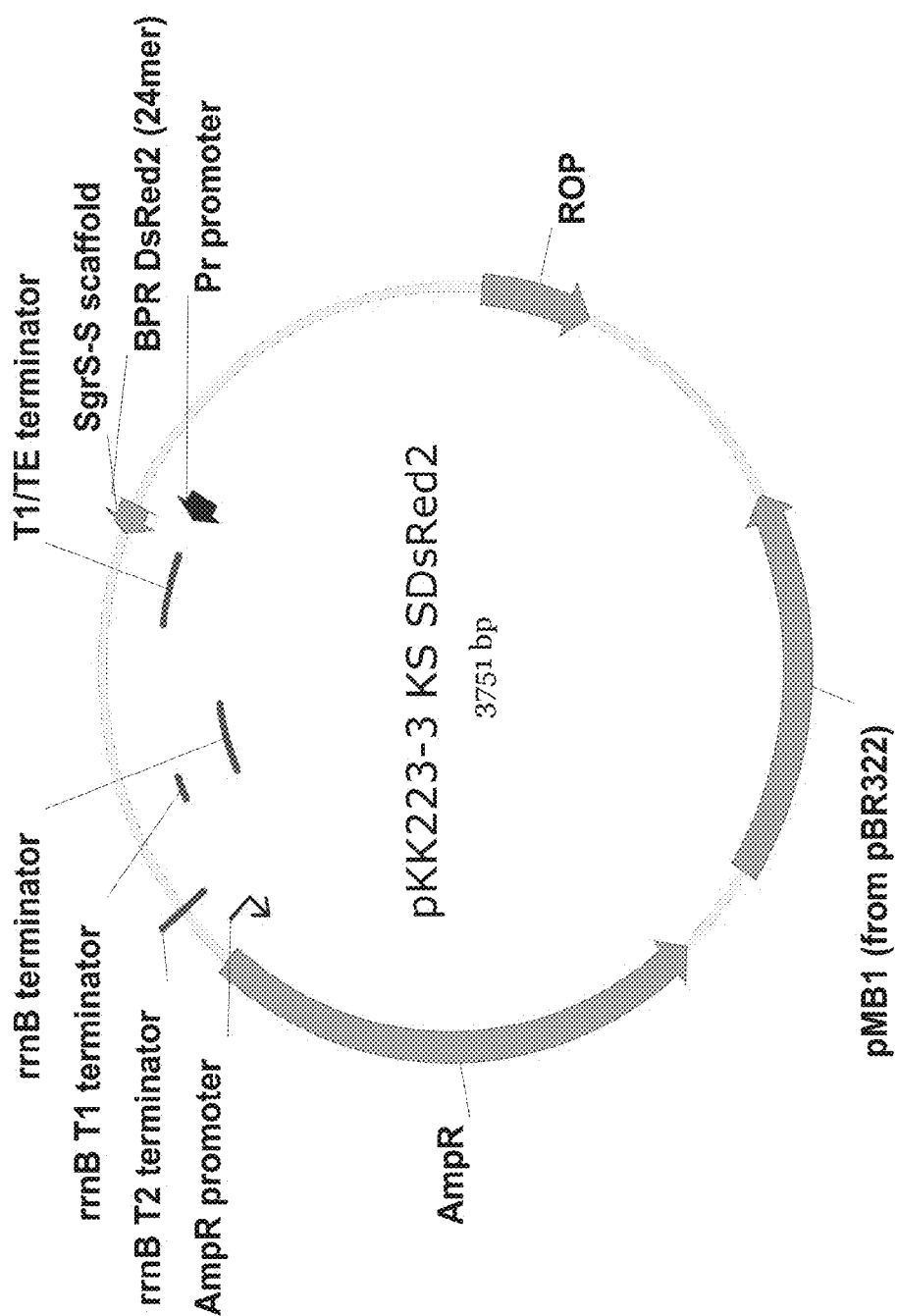
FIG. 1 shows recombination of sRNA including a SgrS scaffold based on a pKK223-3 plasmid which is a commercially available plasmid used for expression of sRNA.

As far as it is not defined in other ways, all technical and scientific terms used in the present specification have the same meaning as being generally appreciated by those skilled in the art to which the present invention pertains. In general, a nomenclature used in the present specification and experimental methods to be described below are well known in technical fields and generally used.

The definitions of the main terms used in the description of the present invention, etc., are described as follows.

Small RNA (hereinafter, referred to as "sRNA") used herein is a short-length RNA usually having 200 or less of base sequences in length, which is not translated into protein and effectively inhibits translation of a specific mRNA through complementary binding.

As used herein, the term "gene" should be considered in the broadest meaning and may encode structural or regulatory proteins. Here, the regulatory protein includes a transcription factor, a heat shock protein or a protein involved in DNA/RNA replication, transcription and/or translation. In the present invention, the target gene to be a target for inhibition of expression may exist as an extrachromosomal component.

In an aspect, the present invention relates to a vector comprising (a) a promoter, (b) a nucleic acid encoding a region that forms complementary base pairs with a target gene mRNA; (c) a wild-type or mutant sRNA scaffold of a nucleic acid encoding an Hfq binding site represented by SEQ ID NO: 91 derived from sRNA of SgrS, and (d) a transcription terminator.

The promoter of the present invention is preferably an inducible promoter that operates only when an inducer is present, a constitutive promoter that always operates, and promoters derived from these promoters (trc promoter or tac promoter). When the activity of these promoters is regulated, an expression level of sRNA is changed, such that it is possible to regulate an expression degree of the target gene. In most of the genes, the expression level of sRNA is controlled by introducing various constitutive promoters, and thus, the expression of the target gene may also be regulated. As the constitutive promoter, various promoters suggested in the Anderson promoter collection (http://partsregistry.org/Promoters/Catalog/Anderson) produced by Chris Anderson may be used.

The promoter of the present invention is preferably selected from a group consisting of trc promoter, tac promoter, Anderson promoter collection as a constitutive promoter, arabinose operon promoter as an inducible promoter, and lactose operon promoter.

The mutant sRNA scaffold of the present invention controls binding affinity between the sRNA and Hfq to fine-tune the expression levels of the target gene. When the expression of genes that are critical to the survival of microorganisms or genes that inhibit a growth rate is inhibited, a system in which sRNA is expressed needs to be constructed only when it is necessary under the inducible promoter. However, when the inducible promoter is introduced, the expression level is not easily controlled. Therefore, in the present invention, preferably, the expression level of the target gene is fine-tuned through mutagenesis of the Hfq binding site.

In the present invention, some sequences of the sRNA scaffold of SgrS (FIG. 2; (SEQ ID NO: 92)) are represented by SEQ ID NO: 91, and mutation is induced. The binding affinity between sRNA and Hfq is regulated by converting GGUG sequences at position Nos: 5 to 8 of SEQ ID NO: 91 which is a first stem region into GGAC, CCUG and CCUC or by converting GGUG 4nt into 6nt and 8nt. Further, it is characterized by converting AAAA sequence at position Nos: 10 to 13 of SEQ ID NO: 91 which is a first loop region of the sRNA scaffold of SgrS into CCGG; CCCC, CCUU, GGGG; GGCC, GGUU, UUGG and UUUU or by converting UAUU sequence at position Nos: 1 to 4 of SEQ ID NO: 91 which is the Hfq binding site into GAUU, UCUU, UACU, UAAU, UAUC, UAUA, GCCC, GCAC, GACC and GAAC. Further, it is characterized by converting a tail length of U at position Nos: 42 to 49 of SEQ ID NO: 91 which is the transcription terminator and Hfq binding site of the sRNA scaffold of SgrS into 4 to 8.

[SEQ ID NO: 91]
5'-UAUUGGUGUAAAAUCACCCGCCAGCAGAUUAUACCUGCUGGUUUUUU
UU-3'

The mutant sRNA scaffold of the present invention is preferably selected from a group consisting of (i) an sRNA scaffold of which one or more base is substituted at positions $1^{st}$ to $4^{th}$ of SEQ ID NO:91 (ii) an sRNA scaffold of which one or more base is substituted at positions $5^{th}$ to $8^{th}$ of SEQ ID NO:91, (iii) an sRNA scaffold of which 2 or 4 bases are inserted into positions 5$^{th}$ to 8$^{th}$ of SEQ ID NO:91, (iv) an sRNA scaffold of which 4 bases are substituted at positions 10$^{th}$ to 13$^{th}$ of SEQ ID NO: 91, and (v) an sRNA scaffold of which 1 to 4 bases are deleted at positions 42$^{nd}$ to 49$^{th}$ of SEQ ID NO:91.

The region that forms complementary binding with the target gene mRNA of the present invention is preferably 10 to 100 bp.

The target gene mRNA of the present invention is preferably selected from a group consisting of DsRed2 (red fluorescence protein), luxR (luxR family transcriptional regulator), araC (arabinose operon regulatory protein), kanR (kanamycin resistance gene), tyrR (DNA-binding transcriptional dual regulator, tyrosine-binding), ppc (phosphoenolpyruvate carboxylase), csrA (carbon storage regulator), pgi (glucose-6-phosphate isomerase), gltA (citrate synthase), accA (acetyl-CoA carboxyltransferase, alpha subunit), accB (biotin-carboxyl carrier protein), accC (acetyl-CoA carboxylase), accD (acetyl-CoA carboxyltransferase, beta-subunit), aceE (pyruvate dehydrogenase E1p component), aceF (pyruvate dehydrogenase), ackA (acetate kinase A), adiY (arginine decarboxylase regulator), argB (acetylglutamate kinase), argC (N-acetylglutamylphosphate reductase), argG (argininosuccinate synthase), argH (argininosuccinate lyase), asnC (AsnC transcriptional regulator), crp (CRP transcriptional dual regulator), csiD (a predicted protein induced by carbon starvation), csiR (carbon starvation induced regulator), cytR (cytidine regulator), dcuA (dicarboxylate transporter), deoB (phosphopentomutase), deoC (deoxyribose-phosphate aldolase), deoR (deoxyribonucleoside regulator), fabH (beta-ketoacyl-ACP synthases 3), fadD (fatty acyl-CoA synthase), fadR (fatty acid metabolism regulator protein), fbp (fructose-1,6-bisphosphatase), fnr (fumarate and nitrate reduction regulatory protein), fruR (fructose operon transcriptional repressor), ftsL (essential cell division protein FtsL), ftsQ (essential cell division protein FtsQ), ftsW (essential cell division protein FtsW), ftsZ (essential cell division protein FtsZ), fur (ferric uptake regulator), gabD (succinate semialdehyde dehydrogenase), gabP (GABA permease), gabT (GABA aminotransferase), gadA (glutamate decarboxylase A subunit), gadB (glutamate decarboxylase B subunit), gadC (GABA APC transporter), glcC (glc operon transcriptional activator), glpK (glycerol kinase), glpR (3-Glycerol-3-phosphate regulon repressor), glpX (fructose 1,6-bisphosphatase II), gltA (citrate synthase), hfld (lysogenization regulator), ihfa (Integration host factor alpha), ihfb (Integration host factor beta), ilvB (acetolactate synthase isozyme 1 large subunit), ilvC (acetohydroxy acid isomeroreductase), ilvD (dihydroxy acid dehydratase), ilvG_1 (acetolactate synthase II, large subunit, N-ter fragment), ilvG_2 (acetolactate synthase II, large subunit, C-ter fragment), ilvH (acetolactate synthase isozyme 3 small subunit), ilvL (ilvGEDA operon leader peptide), ilvM (acetolactate synthase isozyme 2 small subunit), ilvN (acetohydroxybutanoate synthase isozyme 2 small subunit), ilvX (Predicted small protein), lexA (transcription regulator LexA), lpxC (UDP-3-O-acyl-N-acetylglucosamine deacetylase), marA (multiple antibiotic resistance protein MarA), metJ (MetJ transcriptional repressor), modE (transcriptional regulator ModE), nadB (L-aspartate oxidase), narL (nitrate/nitrite response regulator), pck (phosphoenolpyruvate carboxykinase), PdhR (pyruvate dehydrogenase complex regulator), phoP (Transcriptional regulatory protein PhoP), pnuC (PnuC NMN transporter), ppsA (phosphoenolpyruvate synthetase), pta (Phosphate acetyltransferase), purA (adenylosuccinate synthetase), purB (adenylosuccinate lyase), purR (HTH-type transcriptional repressor PurR), puuE (4-aminobutyrate aminotransferase), rbsA (ribose import ATP-binding protein Rbs), rbsB (ribose import ATP-binding protein RbsB), rbsD (ribose pyranose), rbsK (ribokinase), rbsR (ribose operon repressor), rcsB (transcriptional regulatory protein RcsB), rutR (HTH-type transcriptional regulator RutR), serA (D-3-phosphoglycerate dehydrogenase), serC (3-phosphoserine aminotransferase), soxS (regulatory protein SoxS), sroD (SroD small RNA), zwf (glucose 6-phosphate-1-dehydrogenase), asnA (asparagine synthetase A), asnB (asparagine synthetase B), carA (carbamoyl phosphate synthetase A), carB (carbamoyl phosphate synthetase B), ddlB (D-alanine-D-alanine ligase B), deoA (thymidine phosphorylase), deoD (purine nucleoside phosphorylase deoD-type), dpiA (transcriptional regulatory protein DpiA), fis (Fis family transcriptional regulator), gadE (DNA-binding transcriptional activator), gadW (transcriptional regulator GadW), gadX (transcriptional regulator GadX), glpF (glycerol uptake facilitator protein), ilvY (IlvY DNA-binding transcriptional dual regulator), ivbL (ilvB operon leader peptide), lhgO (L-2-hydroxyglutarate oxidase), lpd (Lipoamide dehydrogenase), lrp (Lrp transcriptional dual regulator), metB (O-succinylhomoserine lyase), metL (aspartate kinase), mraY (phospho-N-acetylmuramoyl-pentapeptide transferase), mraZ (transcriptional regulator MraZ), murE (UDP-N-acetylmuramoylalanyl-D-glutamate 2,6-diaminopimelate ligase), murF (D-alanyl-D-alanine-adding enzyme), murG (N-acetylglucosaminyl transferase), nac (nitrogen assimilation regulatory protein), nadA (quinolinate synthase), nsrR (nitrite-sensitive transcriptional repressor), panC (pantothenate synthetase), panD (Aspartate 1-decarboxylase), pgl (6-phosphogluconolactonase), pyrB (aspartate carbamoyltransferase, PyrB subunit), pyrC (dihydroorotase), pyrL (aspartate carbamoyltransferase, PyrI subunit), rob (right origin-binding protein), rpe (ribulose phosphate 3-epimerase), talA (transaldolase A), thrA (homoserine dehydrogenase), thrB (homoserine kinase), thrC (threonine synthase), thrL (thr operon leader peptide), tktA (transketolase I), tktB (transketolase II) and torR (torCAD operon response regulator TorR).

The binding affinity between the sRNA scaffold and Hfq of the present invention is preferably regulated by mutation of sRNA scaffold.

The length of U tail of the transcription terminator is preferably 4 to 8.

In another aspect, the present invention relates to a recombinant microorganism transformed with one of said vectors.

The term "nucleic acid" used herein may refer to RNA, DNA, stabilized RNA or stabilized DNA. Here, "encoding" refers to a nucleic acid sequence encoding the sRNA and complementary to the sRNA.

In the present invention, the "vector" refers to a DNA construct including DNA sequences operably linked to an appropriate controlling sequence capable of expressing DNA in an appropriate host. The vector may be a plasmid, phage particles, or simply be a potential genomic insert. When the vector is transformed in the appropriate host, the vector may replicate and function regardless of the host genome, or in some cases, may be incorporated with the genome itself. The plasmid is the most generally used form of the vector at present, such that the "plasmid" and the "vector" of the present specification are sometimes interchangeably used. For the purpose of the present invention, it is preferable to use a plasmid vector. A typical plasmid vector which is usable for the purpose has a structure including (a) a replication origin for effective replication so as to include several to hundreds of plasmid vectors per a host cell, (b) an antibiotic-resistant gene for selection of the host cell transformed with the plasmid vector, and (c) a restriction enzyme cleavage site into which a foreign DNA fragment is able to be inserted. Even though an appropriate restriction enzyme cleavage site does not exist, ligation between the vector and the foreign DNA may be easily obtained by using a synthetic oligonucleotide adaptor or a linker according to a general method. After the ligation, the vector is required to be transformed into the appropriate host cell. The transformation may be easily achieved by a calcium chloride method or electroporation (Neumann, et al., *EMBO J.*, 1:841, 1982). As the vector which is used for the expression of the sRNA according to the present invention, an expression vector known in the art may be used.

The base sequence of nucleic acid is operably linked when it is arranged in a functional relationship with another nucleic acid sequence. For example, a promoter or an enhancer directly affects transcription of the sequence, and is placed or linked to an appropriate position so as to be operable in a coding sequence; and a ribosomal binding site affects the transcription of the sequence and is linked to the coding sequence so as to be operable in the coding sequence. DNA that encodes a pre-sequence or a secretion leader sequence encodes a pre-protein participating in secretion of polypeptide and is directly linked to the target gene. In general, the term: "operably linked" means that DNA sequences are physically connected. In addition, in the case of the secretion leader sequence, it means contact and existence in a leading frame. However, the enhancer does not need to have a contact. The linkage between these sequences is performed by ligation (linkage) at a convenient restriction enzyme site. When the site does not exist, a synthetic oligonucleotide adaptor or a linker is used according to a conventional method.

In another aspect, the present invention relates to a recombinant microorganism transformed with the vector as described above.

The term "transformation" used herein means that DNA is replicable as a chromosomal extrinsic factor or through chromosomal integration completion by introducing DNA into a host.

It should be understood that all vectors do not equally exert function in expressing the DNA sequences of the present invention. Similarly, all of the host cells do not exert the function equally to the same expression system. However, a person skilled in the art is able to have an appropriate selection of various vectors, expression control sequences, and host without departing from the scope of the present invention with no undue experimental burden. For example, the host needs be considered in selecting the vector, which is because the vector is required to be replicated in the host. Replication numbers of the vector, ability to control the replication numbers, and other proteins encoded by the vector, for example, expression of an antibiotic marker are also required to be considered.

In still another aspect, the present invention relates to a method for fine-tuning mRNA expression level of a target gene by introducing the vector into a prokaryote or expressing the vector in the prokaryote.

The prokaryote in the present invention is selected from a group consisting of *E. Coli., Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus, Clostridium, Corynebacterium, Streptomyces, Bifidobacterium* and *Cyclobacterium*.

In still another aspect, the present invention relates to a method for screening a target gene for production of a target product, the screening method comprising:

(a) fine-tuning an expression level of any one or more genes among genes that are present in a target strain for producing the target product and that participate in a biosynthetic pathway for the target product, according to the above method; and (b) selecting a gene in which expression is regulated as the target gene for production of the target product, when a production yield of the target product is improved by fine-tuning the expression level.

In still another aspect, the present invention relates to a method for improving a target product-producing strain, the method including:

(a) fine-tuning an expression of any one or more genes among genes that are present in a target strain for producing the target product and that participate in a biosynthetic pathway for the target product, according to the above method;

(b) screening a gene in which expression is regulated as a target gene for production of the target product, when a production yield of the target product is improved by fine-tuning the expression; and (c) introducing an expression degree of the screened gene to produce a recombinant strain.

EXAMPLE

Hereinafter, the present invention will be described in more detail with reference to the following Examples. These examples are only for exemplifying the present invention, and it will be obvious to those skilled in the art that the scope of the present invention is not construed to be limited to these examples.

Example 1: Confirmation of Synthetic sRNA Performance 1-1: Construction of Synthetic sRNA and Construction of sRNA Expression Plasmid for Utilization In order to ensure convenience of expression of sRNA, a plasmid as shown in FIG. 1 was constructed. For subsequent experiments, sRNA or a promoter in the plasmid of FIG. 1 was modified by site-directed mutagenesis and used.

Restriction enzymes used in this example and the following examples were purchased from New England BioLabs (U.S.A.) and Enzynomics (Korea), and PCR polymerase was purchased from Solgent (Korea). Primers were purchased from Macrogen (Korea), and other enzymes were purchased from Enzynomics (Korea). Other things were marked separately.

A multiple cloning site of pBluescript II KS+(Stratagene) was subjected to PCR using primers of SEQ ID NOs: 1 and 2 and inserted into HindIII/NaeI site of the pKK223-3 plasmid produced by Pharmacia. The PCR product of the multiple cloning site was digested with PvuII and NaeI, and the plasmid pKK223-3 was digested with HindIII and NaeI. Then, the plasmid pKK223-3 KS was constructed by forming blunt termination using Klenow polymerase and joining two DNA fragments. A Pr promoter and a transcription terminator T1/TE were inserted into the above-constructed plasmid for the sRNA scaffold and an expression thereof, thereby constructing a plasmid for sRNA expression. The sequences of the Pr promoter, the transcription terminator T1/TE and the sRNA scaffold were cloned by PCR using primers of SEQ ID NOs: 3 and 4 in Rlowcat-PrMicC*Ter used in the previous studies (Na, D et al, *Nat Biotechnol.*, 31(2), 170-174, 2013). The PCR product of the Pr promoter-MimC structure-T1/TE transcription terminator was digested with BamHI and NotI, and the pKK223-3 KS was also digested with BamHI/NotI, and these two DNA fragments were ligated. The sequence of the Pr promoter used herein is the sequence of BBa_R0051 registered in the Registry of Standard Biological Parts data (http://parts.igem.org/) and the T1/TE promoter is the sequence of BBa_B0015 in the same database. In the BPR represented as the base pairing region, a 24-mer nucleotide sequence was added from a starting codon of the DsRed2 fluorescent protein. The plasmid as produced above was named pKK223-3 KS Pr MDsRed2. The BPR was inserted by inverse PCR using the primers of SEQ ID NOs: 5 and 6. The sequence of the scaffold of the SgrS sequence was shown in FIG. 2 (SEQ ID NO: 92), and was also produced by the inverse PCR using the primers of SEQ ID NOs: 7 and 8. The plasmid as produced above was named pKK223-3 KS Pr SDsRed2. The map of the plasmid having the SrgS sequence was shown in FIG. 1, and an *E. coli* strain DH5a was used for construction of the plasmid.

<Primer Sequence Used>

[SEQ ID NO. 1]
5'-GGCCAATTCAGCTGGTACCGGGCCCCCCCTCG-3'

[SEQ ID NO. 2]
5'-GGCCAATTGCCGGCGAGCTCCACCGCGGTGG-3'

[SEQ ID NO. 3]
5'-GGCCTTAAGCGGCCGCTAACACCGTGCGTGTTGAC-3'

[SEQ ID NO. 4]
5'-CCGGAATTGGATCCTATAAACGCAGAAAGGCCC-3'

[SEQ ID NO. 5]
5'-CTCGCCATATATTTGTCTTTCTGTTGGGCCATTGCATTGC-3'

[SEQ ID NO. 6]
5'-CAGTGAGAACGTCATGCAACCATTATCACCGCCAGAGG-3'

[SEQ ID NO. 7]
5'-GCCAGCAGATTATACCTGCTGGTTTTTTTTCTCGAGCCAGGCATCAA

ATAAAACG-3'

[SEQ ID NO. 8]
5'-GGGTGATTTTACACCAATAGACAAATATATGGCGAGCAGTGAGAACG

TCATGCAACCATTATCACCGCCAGAGG-3'

Figure 3:
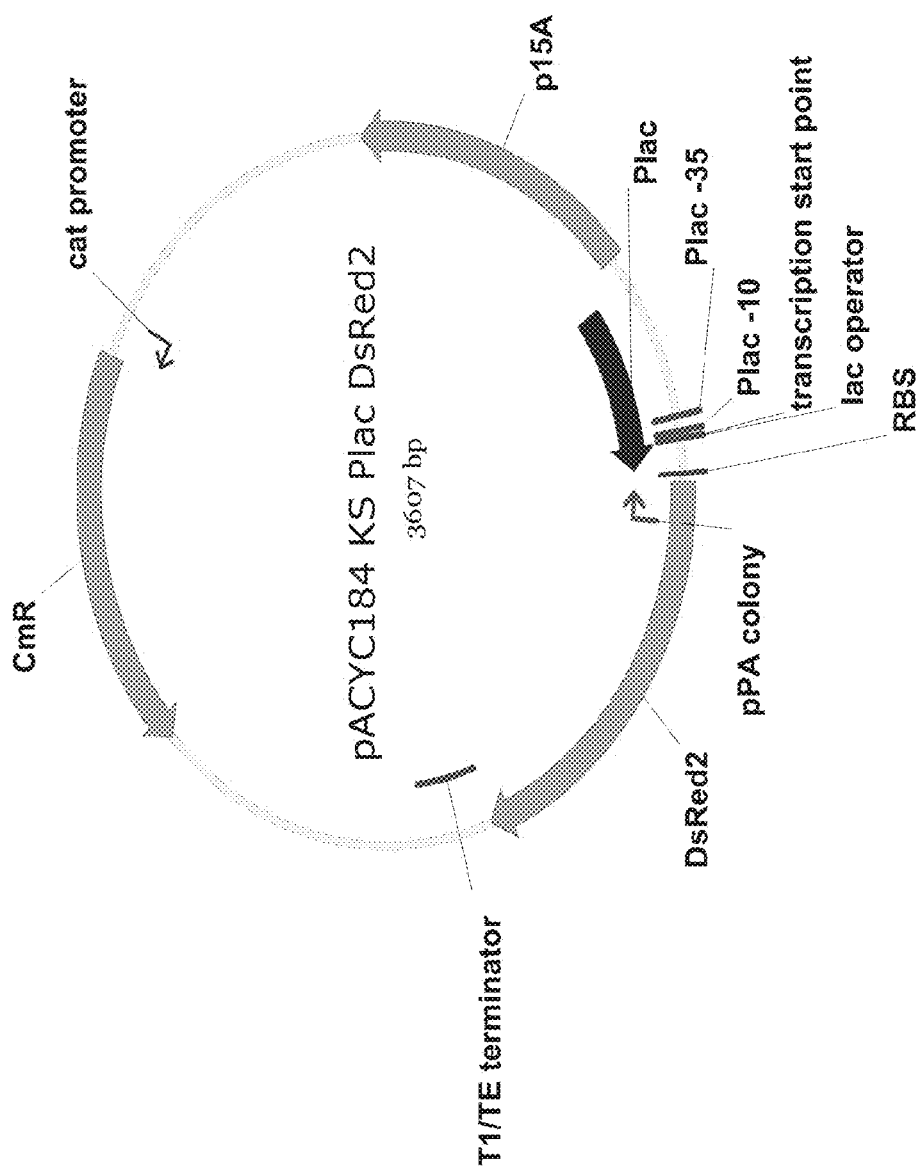
FIG. 3 shows recombination for expression of DsRed2 gene based on a pACYC184 plasmid which is a commercially available plasmid used for expression of sRNA target gene.

1-2: Construction of Target Gene Plasmid for Investigation of Synthetic sRNA Performance A fluorescent protein DsRed2 was selected as a target gene for easily confirming the performance of the sRNA, and a reporter plasmid as shown in FIG. 3 was constructed for expression of the DsRed2 gene. A multiple cloning site of pBluescript II KS+(Stratagene) was subjected to PCR using primers of SEQ ID NOs: 1 and 2 and inserted into XbaI/NaeI site of the pACYC184 (New England BioLabs, U.S.A.) plasmid produced by Pharmacia. The PCR product of the multiple cloning site was digested with PvuII and NaeI, and the plasmid pACYC184 was digested with XbaI and NaeI. Then, the plasmid pACYC184 KS was constructed by forming blunt termination using Klenow polymerase and ligating two DNA fragments. A plasmid having a fluorescent protein as a target gene of sRNA was constructed. The lactose promoter, the fluorescent protein DsRed2 gene, and the T1/TE sequence as the transcription terminator were inserted into the ApaI/SalI site of the multiple cloning site. The lactose promoter, the DsRed2 gene, and the T1/TE transcription terminator used herein were constructed by PCR using SEQ ID NOs: 9 and 10 in Rlowcat-Plac-DsRed2 used in the previous study (Na, D et al, *Nat Biotechnol.*, 31(2), 170-174, 2013). The lactose promoter was constructed by PCR using pBluescript SK+ (Stratagene) as a template, and the DsRed2 gene was constructed by PCR using pDsRed2-N1 (Clontech) as a template. The T1/TE transcription terminator is the BBaR0015 sequence registered in the above Registry of Standard Biological Parts database (http://parts.igem.org/). *E. coli* DH5a was used for construction of the plasmid.

<Primer Sequence Used>

[SEQ ID NO. 9]
5'-GGCCTTAAGGGCCCGTGGATAACCGTATTACCGC-3'

[SEQ ID NO. 10]
5'-CCGGAATTGTCGACTATAAACGCAGAAAGGCCC-3'

1-3: Investigation of Synthetic sRNA Performance

Figure 4:
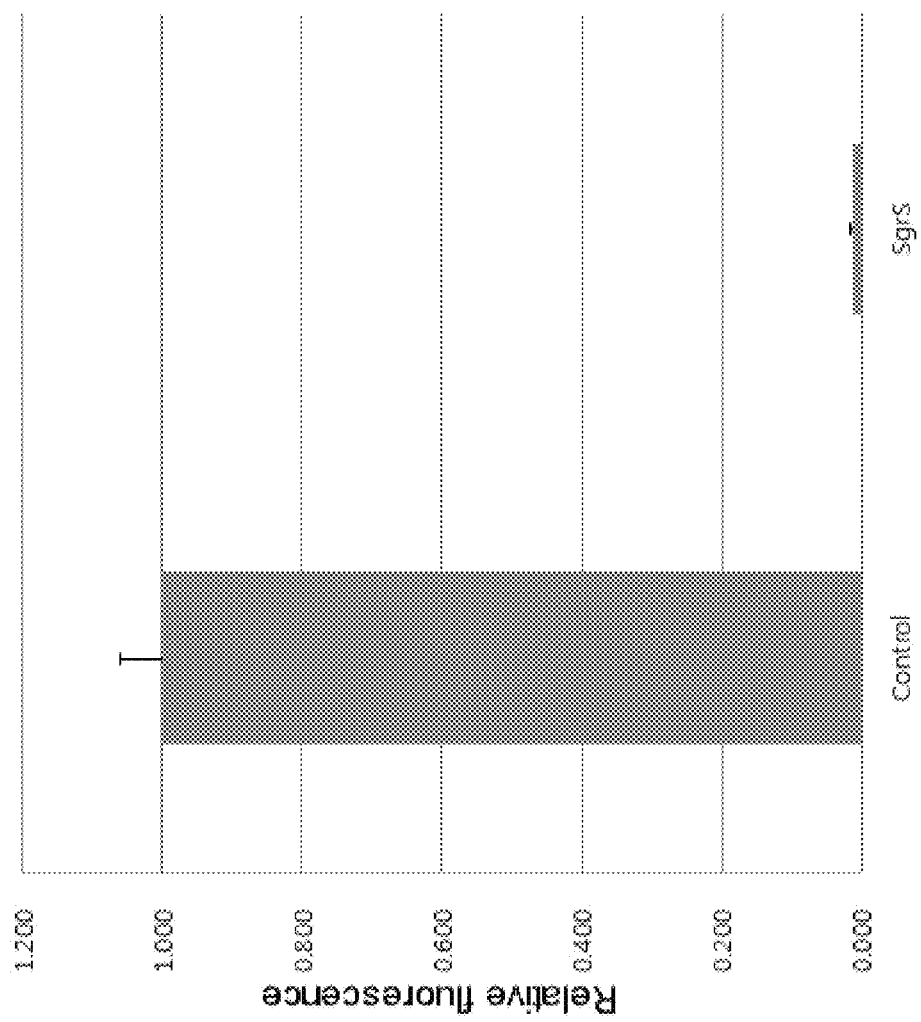
FIG. 4 shows that the synthetic sRNA including the SgrS scaffold effectively represses the expression of DsRed2.

An experiment for investigating an expression inhibitory performance of target gene by sRNA was conducted using the above-constructed plasmid. The reporter plasmid constructed in Example 1-2 and the plasmid having the SgrS scaffold and having sRNA including DsRed2 as the target protein constructed in Example 1-1 were simultaneously transformed into DH5a. Then, colonies having both plasmids were selected using LB plates containing Ampicillin (Ap) and Chrolamphenicol (Cm) antibiotics, and then inoculated on the LB medium containing the Ap and the Cm. Then, the strains were cultured up to stationary phase and whether the fluorescence was expressed was measured. As shown in FIG. 4, the anti-DsRed2 synthetic sRNA having the SgrS scaffold showed 99% expression inhibitory efficiency as compared to the control group. All of the two strains had pACYC184 KS Plac DsRed2, and the control group and the SgrS strain had pKK223-3 KS and pKK223-3 KS SDsRed2, respectively. The control group for fluorescence measurement, a strain having pACYC184 KS and pKK223-3 KS was used.

1-4: Investigation of Specificity of Synthetic sRNA

Figure 5:
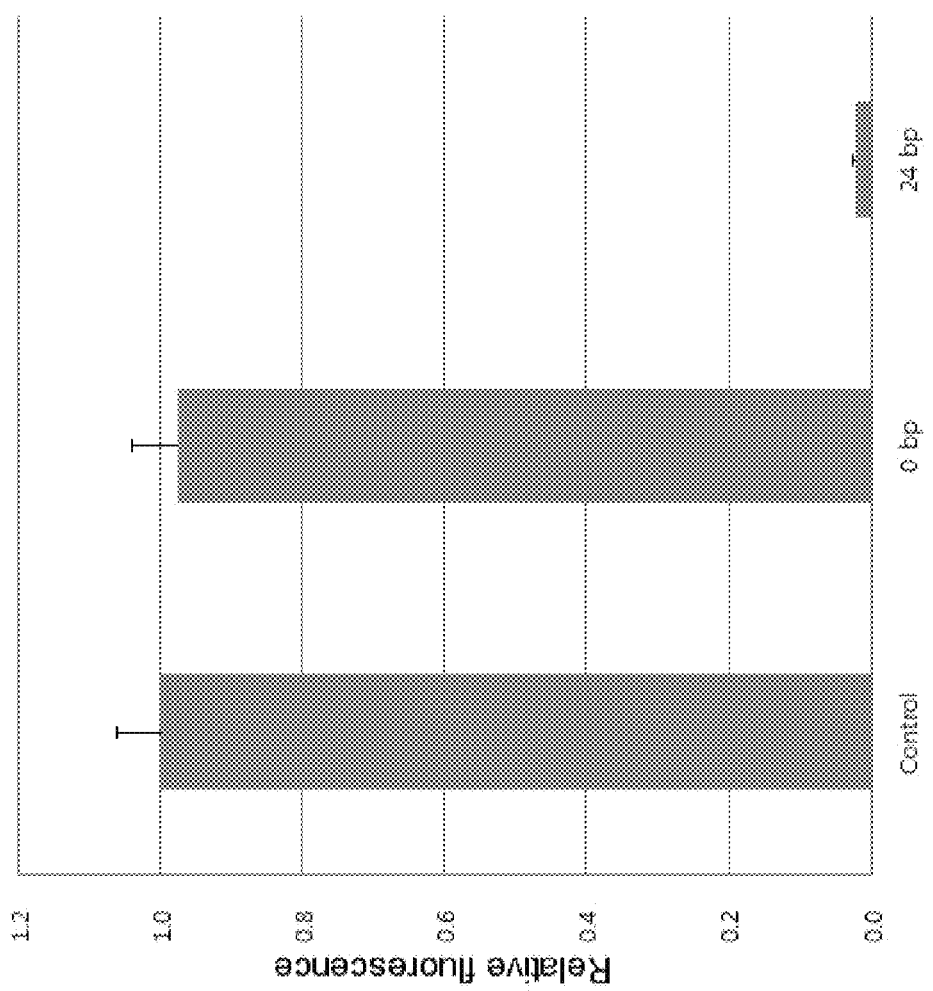
FIG. 5 shows that a repression ability of synthetic sRNA targeting the DsRed2 is caused by a base pairing region (BPR).

The experiment was conducted to confirm whether the expression inhibition of the target gene by sRNA was specifically achieved by the BPR. In this experiment, a plasmid (pKK223-3 KS SDsRed2) having sRNA having a SgrS scaffold and including a BPR consisting of 24 nucleotides was used. The plasmid without BPR was constructed using pKK223-3 KS SDsRed2 as a template and primers of SEQ ID NOs: 11 and 12 through inverse PCR, which was named pKK223-3 KS SO. This was used for the sample labeled non-targeting sRNA in the following data. In addition, the experiment was conducted in the same manner as in Example 1-3. The results were shown in FIG. 5. The sRNA without the BPR showed 2% expression inhibitory efficiency of fluorescent protein as compared to the control group, and the sRNA with BPR consisting of 24 nucleotides showed 98% expression inhibitory efficiency of fluorescent protein. This shows that the specific gene was inhibited by the BPR rather than by the synthetic sRNA scaffold.

<Primer Sequence Used>

[SEQ ID NO. 11]
5'-TATTGGTGTAAAATCACCCGCCAGCAG-3'

[SEQ ID NO. 12]
5'-GCAACCATTATCACCGCCAGAGG-3'

Figure 6:
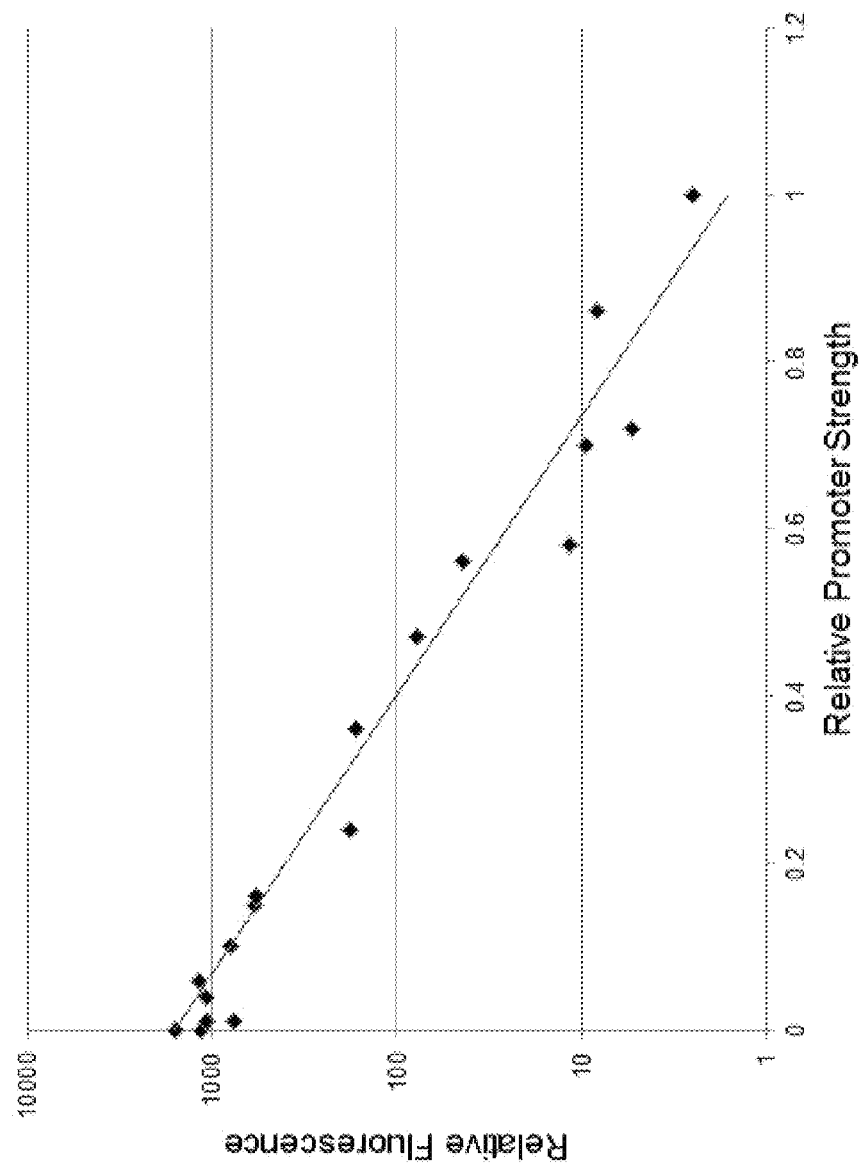
FIG. 6 is a graph showing log values of an effect of inhibiting the target gene expression is linearly proportional to an expression level of sRNA.

Example 2: Regulation of sRNA Expression Through Introduction of Various Promoters and Effects Thereof An experiment for fine-tuning the target gene inhibition was conducted by regulating the expression level of sRNA using a promoter showing various gene expression intensities. The plasmid and experimental method of Example 1 were used, and the promoter of sRNA was cloned by using the inverse PCR, and the promoters of Anderson promoter collection were cloned using primers of SEQ ID NOs. 13 to 46. The SgrS was used as the sRNA scaffold, and the promoters were J23100, J23101, J23102, J23103, J23104, J23105, J23106, J23107, J23109, J23111, J23112, J23113, J23114, J23115, J23116, J23117, and J23118. The results were shown in FIG. 6, and it could be appreciated that the intensity of the promoter was proportional to log values of protein inhibition efficiency.

<Primer Sequence Used for Cloning of Promoter>

J23100:
[SEQ ID NO. 13]
5'-GACTGAGCTAGCCGTCAAGCGGCCGCCACCGCGGTGGAGC-3'

[SEQ ID NO. 14]
5'-CTAGGTACAGTGCTAGCGATGACGTTCTCACTGCTCGCC-3'

J23101:
[SEQ ID NO. 15]
5'-CTAGGTATTATGCTAGCGATGACGTTCTCACTGCTCGCC-3'

[SEQ ID NO. 16]
5'-GACTGAGCTAGCTGTAAAGCGGCCGCCACCGCGGTGGAGC-3'

J23102:
[SEQ ID NO. 17]
5'-CTAGGTACTGTGCTAGCGATGACGTTCTCACTGCTCGCC-3'

[SEQ ID NO. 18]
5'-GACTGAGCTAGCTGTCAAGCGGCCGCCACCGCGGTGGAGC-3'

J23103:
[SEQ ID NO. 19]
5'-CTAGGGATTATGCTAGCGATGACGTTCTCACTGCTCGCC-3'

[SEQ ID NO. 20]
5'-GACTGAGCTAGCTATCAGGCGGCCGCCACCGCGGTGGAGC-3'

J23104:
[SEQ ID NO. 21]
5'-CTAGGTATTGTGCTAGCGATGACGTTCTCACTGCTCGCC-3'

[SEQ ID NO. 22]
5'-GACTGAGCTAGCTGTCAAGCGGCCGCCACCGCGGTGGAGC-3'

J23105:
[SEQ ID NO. 23]
5'-GACTGAGCTAGCCGTAAAGCGGCCGCCACCGCGGTGGAGC-3'

[SEQ ID NO. 24]
5'-CTAGGTACTATGCTAGCGATGACGTTCTCACTGCTCGC-3'

J23106:
[SEQ ID NO. 25]
5'-CTAGGTATAGTGCTAGCGATGACGTTCTCACTGCTCGCC-3'

[SEQ ID NO. 26]
5'-GACTGAGCTAGCCGTAAAGCGGCCGCCACCGCGGTGGAGC-3'

J23107:
[SEQ ID NO. 27]
5'-CTAGGTATTATGCTAGCGATGACGTTCTCACTGCTCGCC-3'

[SEQ ID NO. 28]
5'-GGCTGAGCTAGCCGTAAAGCGGCCGCCACCGCGGTGGAGC-3'

J23109:
[SEQ ID NO. 29]
5'-GACTGAGCTAGCTGTAAAGCGGCCGCCACCGCGGTGGAGC-3'

[SEQ ID NO. 30]
5'-CTAGGGACTGTGCTAGCGATGACGTTCTCACTGCTCGC-3'

J23111:
[SEQ ID NO. 31]
5'-CTAGGTATAGTGCTAGCGATGACGTTCTCACTGCTCGCC-3'

[SEQ ID NO. 32]
5'-GACTGAGCTAGCCGTCAAGCGGCCGCCACCGCGGTGGAGC-3'

J23112:
[SEQ ID NO. 33]
5'-CTAGGGATTATGCTAGCGATGACGTTCTCACTGCTCGCC-3'

[SEQ ID NO. 34]
5'-GACTGAGCTAGCTATCAGGCGGCCGCCACCGCGGTGGAGC-3'

J23113:
[SEQ ID NO. 35]
5'-CTAGGGATTATGCTAGCGATGACGTTCTCACTGCTCGCC-3'

[SEQ ID NO. 36]
5'-GACTGAGCTAGCCATCAGGCGGCCGCCACCGCGGTGGAGC-3'

J23114:
[SEQ ID NO. 37]
5'-GACTGAGCTAGCCATAAAGCGGCCGCCACCGCGGTGGAGC-3'

[SEQ ID NO. 38]
5'-CTAGGTACAATGCTAGCGATGACGTTCTCACTGCTCGC-3'

J23115:
[SEQ ID NO. 39]
5'-CTTGGTACAATGCTAGCGATGACGTTCTCACTGCTCGCC-3'

[SEQ ID NO. 40]
5'-GGCTGAGCTAGCTATAAAGCGGCCGCCACCGCGGTGGAGC-3'

J23116:
[SEQ ID NO. 41]
5'-CTAGGGACTATGCTAGCGATGACGTTCTCACTGCTCGCC-3'

[SEQ ID NO. 42]
5'-GACTGAGCTAGCTGTCAAGCGGCCGCCACCGCGGTGGAGC-3'

J23117:
[SEQ ID NO. 43]
5'-CTAGGGATTGTGCTAGCGATGACGTTCTCACTGCTCGCC-3'

[SEQ ID NO. 44]
5'-GACTGAGCTAGCTGTCAAGCGGCCGCCACCGCGGTGGAGC-3'

J23118:
[SEQ ID NO. 45]
5'-CTAGGTATTGTGCTAGCGATGACGTTCTCACTGCTCGCC-3'

[SEQ ID NO. 46]
5'-GACTGAGCTAGCCGTCAAGCGGCCGCCACCGCGGTGGAGC-3'

Example 3: Minute Regulation of Target Gene Inhibition Through Mutation of sRNA Scaffold An experiment for fine-tuning the target gene inhibition was conducted by mutagenesis on the sRNA scaffold to change the activity thereof. The plasmid and experimental method of Example 1 were used, and the promoter of sRNA was J23105, which showed a 74% inhibition rate in the previous experiment. J23108 was used only in the experiment of FIG. 8. The plasmid expressing sRNA with the J23108 promoter was constructed by the inverse PCR using SEQ ID NOs: 51 and 52. Then, the scaffold was mutated by the inverse PCR using primers of the sequences listed below. The control groups were pKK223-3 KS without the sRNA scaffold and pKK223-3 KS SO without the BPR. All of the sequence mutation of the stem (FIG. 7), the change in stem length (FIG. 8), the sequence of loop (FIG. 9), the mutation of the UAUU sequence (FIG. 10), and the length of U tail (FIG. 11) in the stem loop of the mRNA SgrS scaffold could weaken or strengthen sRNA activity. The U tail is also the transcription terminator and the Hfq binding site. It is thought that the combination of these mutations may further weaken or strengthen the inhibitory activity of sRNA.

Figure 7:
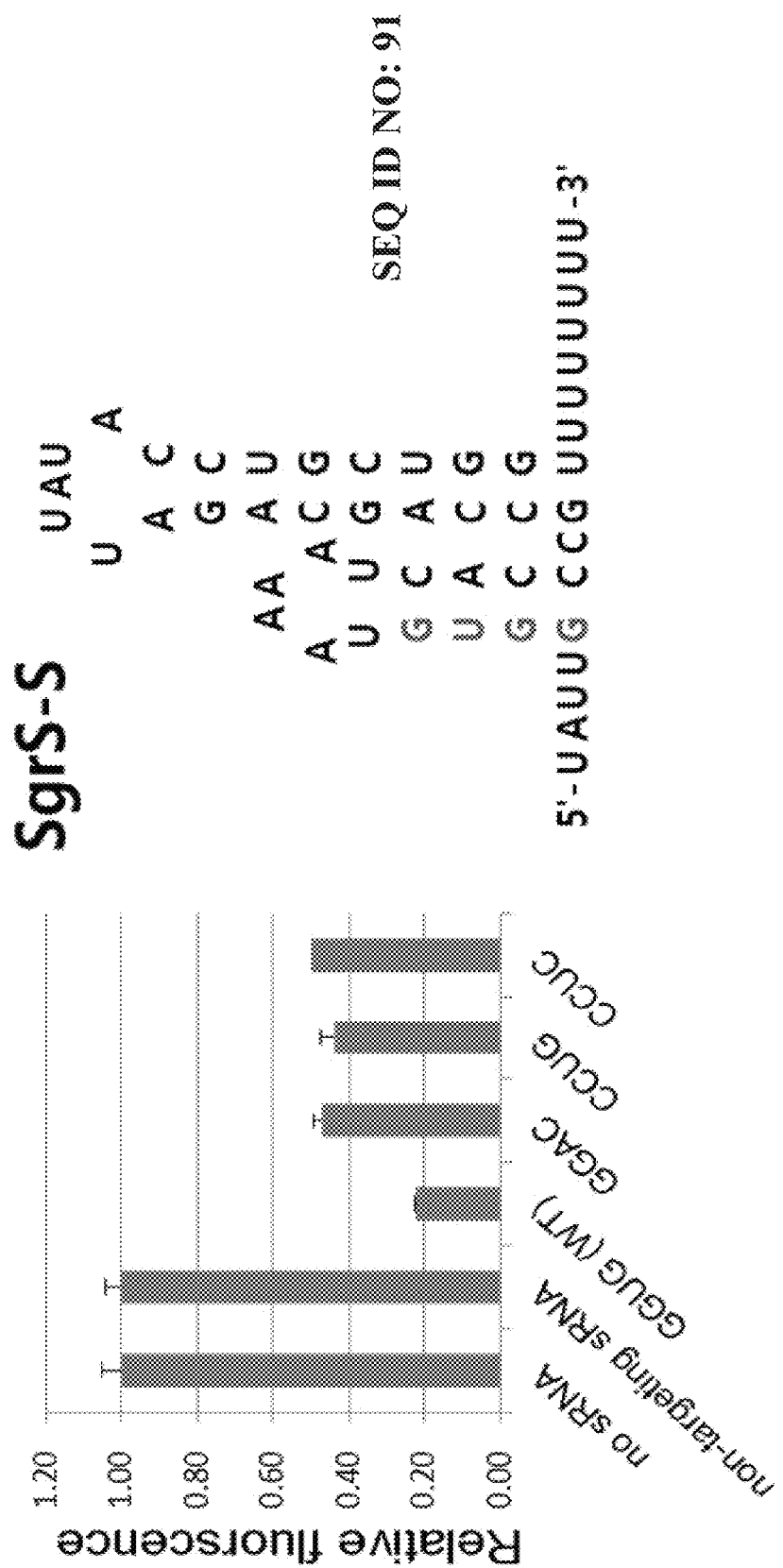
FIG. 7 shows changes in the sRNA expression inhibitory activity according to a sequence change of stem in a stem loop of the Hfq binding site.

<Primer Sequence Used in Mutation Shown in FIG. 7>
Commonly Used Primer:

```
                                        [SEQ ID NO. 47]
5'-AATCACCCGCCAGCAGATTATACCTGCTGG-3'
```

GGAC:
```
                                        [SEQ ID NO. 48]
5'-TTAGTCCAATAATGGCGAGCAGTGAGAAC-3'
```

CCUG:
```
                                        [SEQ ID NO. 49]
5'-TTACAGGAATAATGGCGAGCAGTGAGAAC-3'
```

CCUC
```
                                        [SEQ ID NO. 50]
5'-TTAGTGGAATAATGGCGAGCAGTGAGAAC-3'
```

Figure 8:
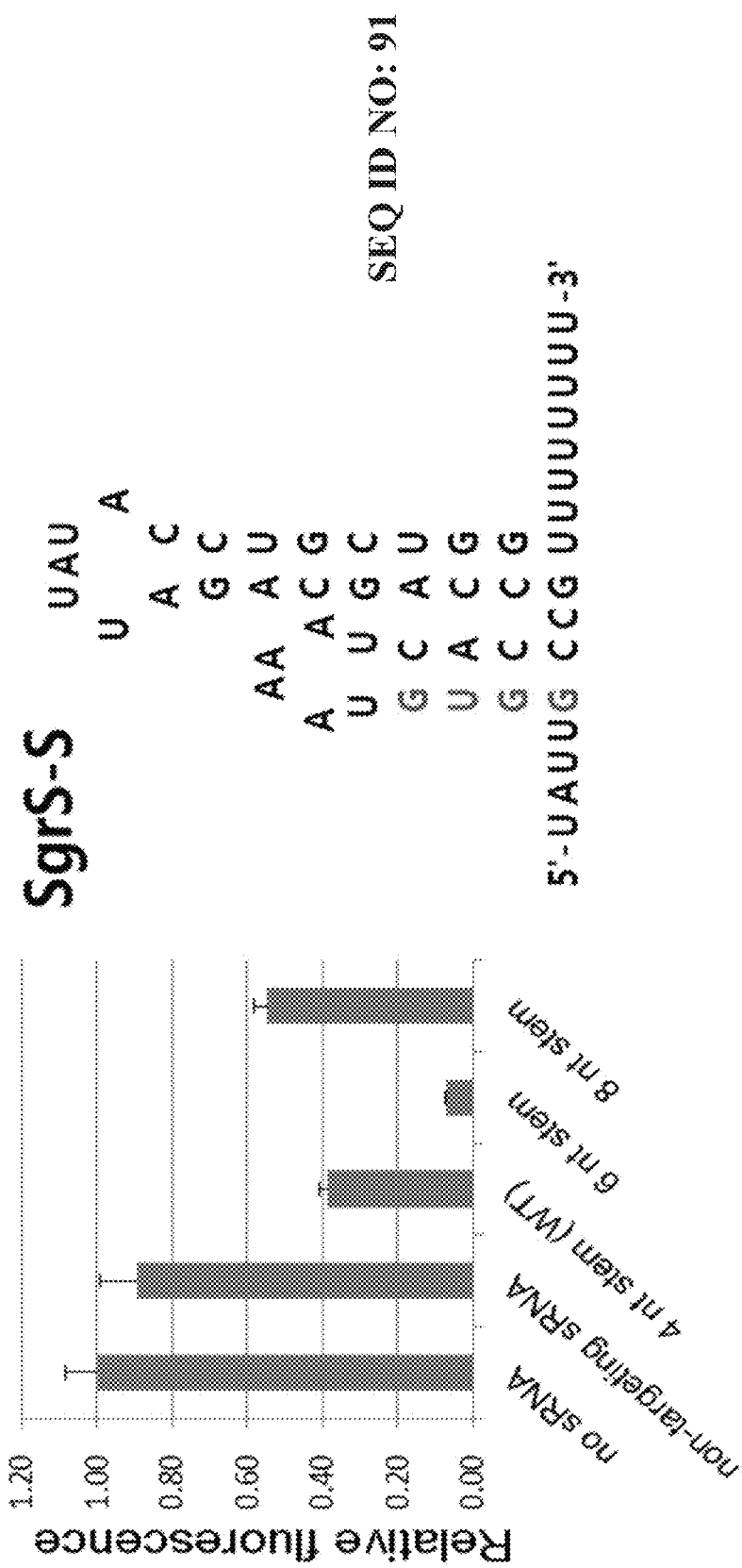
FIG. 8 shows changes in the sRNA expression inhibitory activity according to a length change of stem in the stem loop of the Hfq binding site.

<Primer Sequence Used in Mutation Shown in FIG. 8>
J23108 Construction Primer

```
                                        [SEQ ID NO. 51]
5'-GACTGAGCTAGCTGTCAGGCGGCCGCCACCGCGGTGGAGC-3'

[SEQ ID NO. 52]
5'-CTAGGTATAATGCTAGCGATGACGTTCTCACTGCTCGCC-3'
```

6nt stem:
```
                                        [SEQ ID NO. 53]
5'-TTACCCACCAATAATGGCGAGCAGTGAGAAC-3'

[SEQ ID NO. 54]
5'-AATCCCACCCGCCAGCAGATTATACCTGCTGG-3'
```

8nt stem:
```
                                        [SEQ ID NO. 55]
5'-TTACCCCCACCAATAATGGCGAGCAGTGAGAAC-3'

[SEQ ID NO. 56]
5'-AATCCCCCACCCGCCAGCAGATTATACCTGCTGG-3'
```

Figure 9:
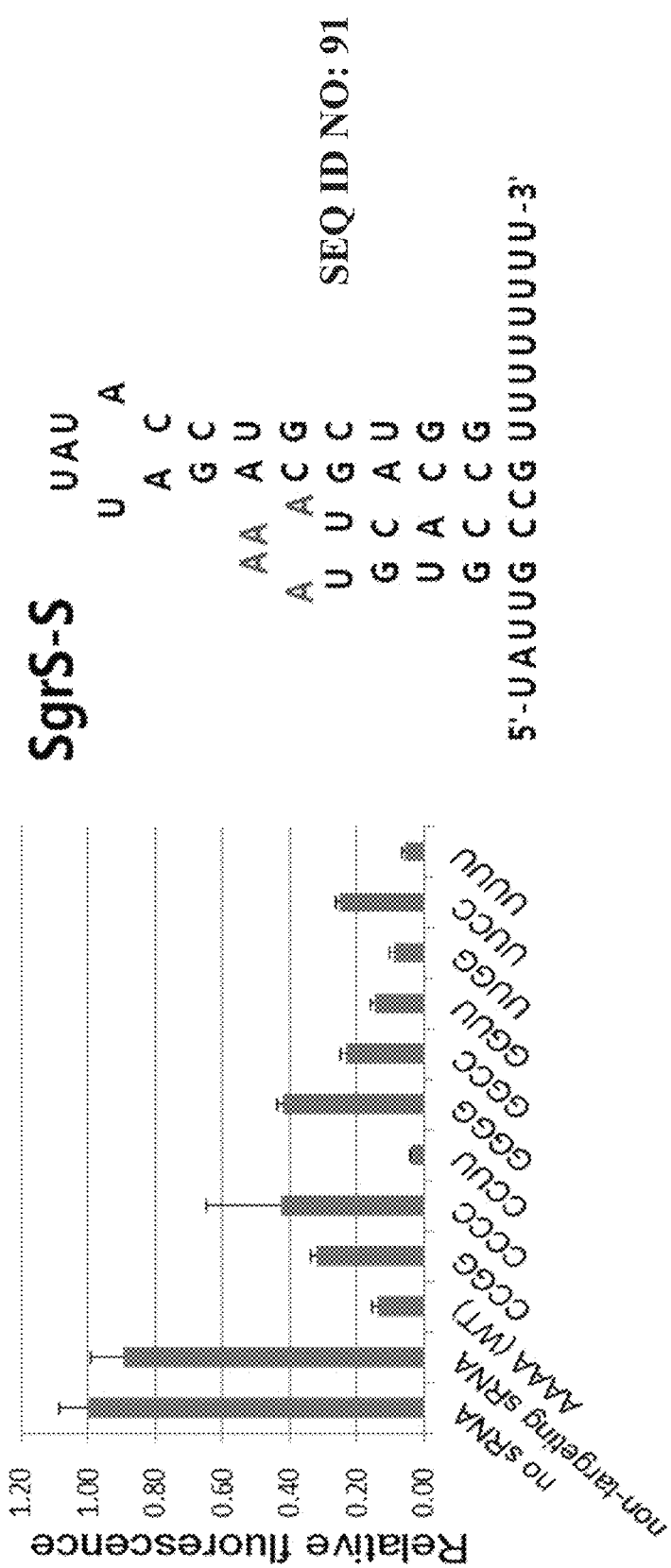
FIG. 9 shows changes in the sRNA expression inhibitory activity according to a sequence change of loop in the stem loop of the Hfq binding site.

<Primer Sequence Used in Mutation Shown in FIG. 9>

CCGG:
```
                                        [SEQ ID NO. 57]
5'-GGACACCAATAATGGCGAGC-3'

[SEQ ID NO. 58]
5'-GGTCACCCGCCAGCAGATTATAC-3'
```

CCCC:
```
                                        [SEQ ID NO. 59]
5'-GGACACCAATAATGGCGAGC-3'

[SEQ ID NO. 60]
5'-CCTCACCCGCCAGCAGATTATAC-3'
```

CCUU:
```
                                        [SEQ ID NO. 61]
5'-GGACACCAATAATGGCGAGC-3'

[SEQ ID NO. 62]
5'-TTTCACCCGCCAGCAGATTATAC-3'
```

GGGG:
```
                                        [SEQ ID NO. 63]
5'-CCACACCAATAATGGCGAGC-3'

[SEQ ID NO. 64]
5'-GGTCACCCGCCAGCAGATTATAC-3'
```

GGCC:
```
                                        [SEQ ID NO. 65]
5'-CCACACCAATAATGGCGAGC-3'

[SEQ ID NO. 66]
5'-CCTCACCCGCCAGCAGATTATAC-3'
```

GGUU:
```
                                        [SEQ ID NO. 67]
5'-CCACACCAATAATGGCGAGC-3'

[SEQ ID NO. 68]
5'-TTTCACCCGCCAGCAGATTATAC-3'
```

UUGG:
```
                                        [SEQ ID NO. 69]
5'-AAACACCAATAATGGCGAGC-3'

[SEQ ID NO. 70]
5'-GGTCACCCGCCAGCAGATTATAC-3'
```

UUCC:
```
                                        [SEQ ID NO. 71]
5'-AAACACCAATAATGGCGAGC-3'

[SEQ ID NO. 72]
5'-CCTCACCCGCCAGCAGATTATAC-3'
```

UUUU:
```
                                        [SEQ ID NO. 73]
5'-AAACACCAATAATGGCGAGC-3'

[SEQ ID NO. 74]
5'-TTTCACCCGCCAGCAGATTATAC-3'
```

Figure 10:
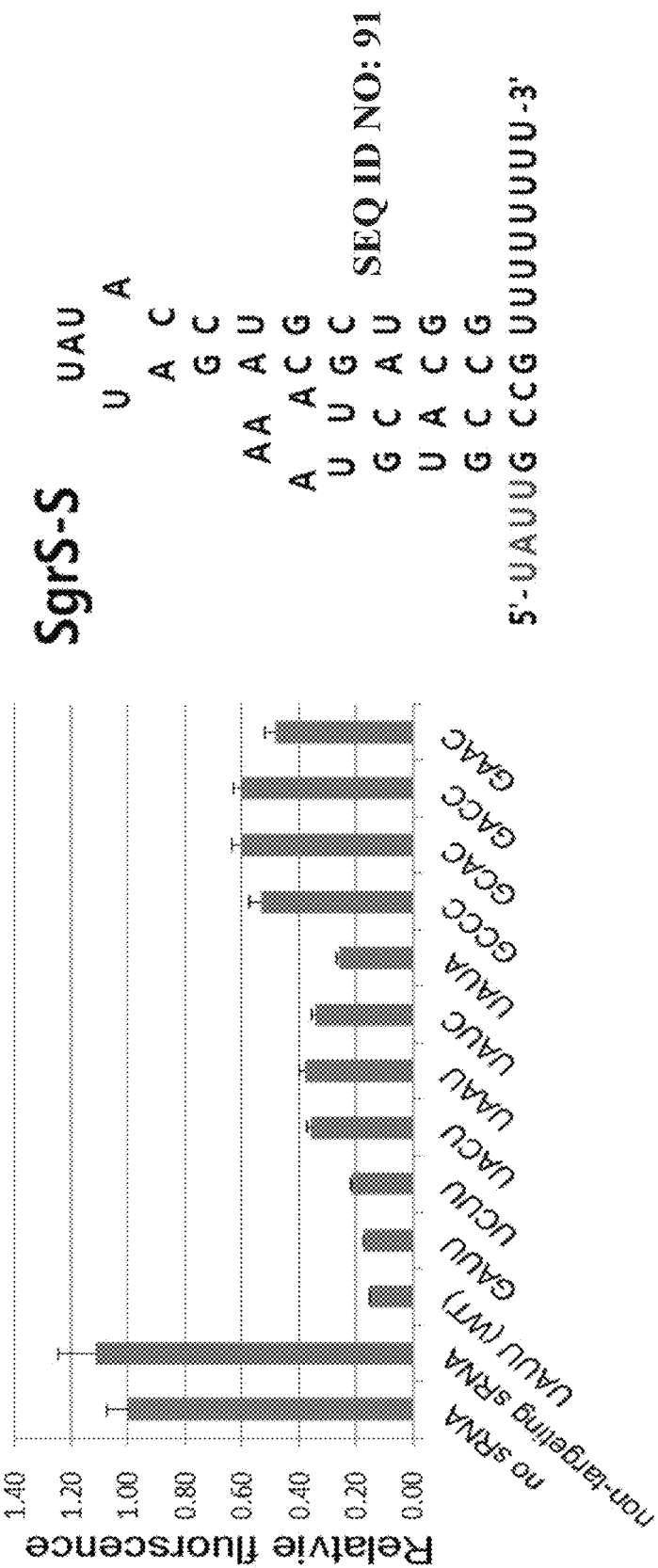
FIG. 10 shows changes in the sRNA expression inhibitory activity according to UAUU sequence change of the Hfq binding site.

<Primer Sequence Used in Mutation Shown in FIG. 10>
Commonly Used Primer:

```
                                        [SEQ ID NO. 75]
5'-GACAAATATATGGCGAGCAG-3'
```

GAUU:
```
                                        [SEQ ID NO. 76]
5'-GATTGGTGTAAAATCACCCGCCAGCAG-3'
```

UCUU:
```
                                        [SEQ ID NO. 77]
5'-GTCTTGGTGTAAAATCACCCGCCAGCAG-3'
```

UACU:
```
                                        [SEQ ID NO. 78]
5'-TACTGGTGTAAAATCACCCGCCAGCAG-3'
```

UAAU:
```
                                        [SEQ ID NO. 79]
5'-TAATGGTGTAAAATCACCCGCCAGCAG-3'
```

UAUC:
```
                                        [SEQ ID NO. 80]
5'-TATCGGTGTAAAATCACCCGCCAGCAG-3'
```

UAUA:
```
                                        [SEQ ID NO. 81]
5'-TATAGGTGTAAAATCACCCGCCAGCAG-3'
```

GCCC:
[SEQ ID NO. 82]
5'-GCCCGGTGTAAAATCACCCGCCAGCAG-3'

GCAC:
[SEQ ID NO. 83]
5'-GCACGGTGTAAAATCACCCGCCAGCAG-3'

GACC:
[SEQ ID NO. 84]
5'-GACCGGTGTAAAATCACCCGCCAGCAG-3'

GAAC:
[SEQ ID NO. 85]
5'-GACCGGTGTAAAATCACCCGCCAGCAG-3'

Figure 11:
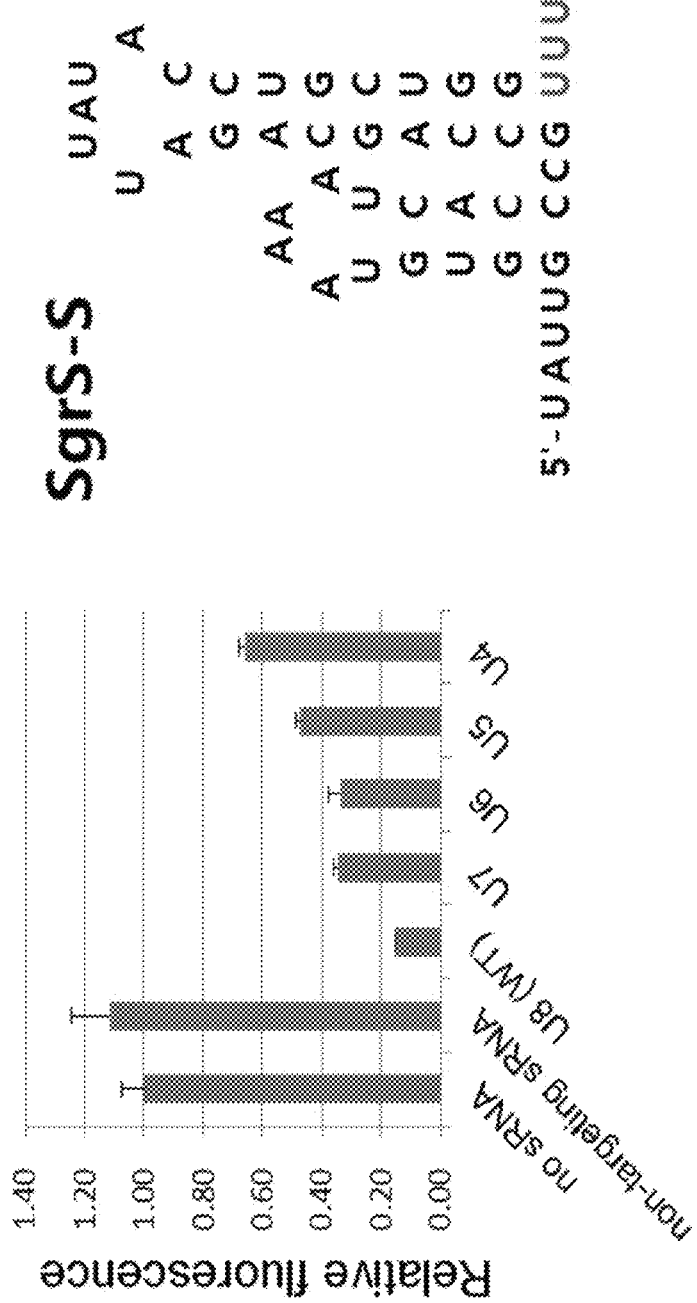
FIG. 11 shows changes in the sRNA expression inhibitory activity according to a length change of a U tail which is the transcription terminator and the Hfq binding site.

<Primer Sequence Used in Mutation Shown in FIG. 11>
Commonly Used Primer:

[SEQ ID NO. 86]
5'-CTCGAGCCAGGC-3'

U7:
[SEQ ID NO. 87]
5'-AAAAAAACCAGCAGGTATAATCTGCTGGCG-3'

U6:
[SEQ ID NO. 88]
5'-AAAAAACCAGCAGGTATAATCTGCTGGCG-3'

U5:
[SEQ ID NO. 89]
5'-AAAAACCAGCAGGTATAATCTGCTGGCG-3'

U4:
[SEQ ID NO. 90]
5'-AAAACCAGCAGGTATAATCTGCTGGCG-3'

INDUSTRIAL APPLICABILITY

The method for fine tuning gene expression levels using a synthetic regulatory sRNA according to the present invention, is capable of fine-tuning the degree of inhibiting the expression of a target gene by regulating the expression level of sRNA or the binding affinity between the sRNA and Hfq, and thus, it is possible to simultaneously, easily, and quickly apply various target gene combinations to various strains without gene deletion through the synthetic regulatory sRNA for regulating gene expression and is therefore very suitable for measuring the metabolizability of each strain and selecting an optimum strain. The method has advantages of easily and quickly selecting the target gene inhibiting the gene expression and expressing the gene selected as above to a desired degree, which is significantly usable in producing recombinant strains for efficient production of various metabolites and establishing an efficient production method, and thus, the method is very useful.

The specific embodiments of the present invention are described in detail as set forth above. However, it will be apparent to those skilled in the art that the specific description is merely desirable exemplary embodiment and should not be construed as limiting the scope of the present invention. Therefore, the substantial scope of the present invention will be defined by the accompanying claims and their equivalents.

The invention claimed is:

1. A vector comprising (a) a promoter, (b) a nucleic acid encoding a region that forms complementary base pairs with a target gene mRNA; (c) a mutant sRNA scaffold of a nucleic acid encoding a Hfq binding site represented by SEQ ID NO: 91 derived from sRNA of SgrS, and (d) a rho independent transcription terminator as represented by positions 19$^{th}$ to 49$^{th}$ of SEQ ID NO: 91, wherein binding affinity between the mutant sRNA scaffold and a Hfq is regulated by mutation of sRNA scaffold.

2. The vector of claim 1, wherein the mutant sRNA scaffold is selected from a group consisting of (i) an sRNA scaffold of which one or more base is substituted at positions 1st to 4th of SEQ ID NO:91 (ii) an sRNA scaffold of which one or more base is substituted at positions 5th to 8th of SEQ ID NO:91, (iii) an sRNA scaffold of which 2 or 4 bases are inserted into positions 5th to 8th of SEQ ID NO:91, (iv) an sRNA scaffold of which 4 bases are substituted at positions 10th to 13th of SEQ ID NO: 91, and (v) an sRNA scaffold of which 1 to 4 bases are deleted at positions 42nd to 49th of SEQ ID NO:91.

3. The vector of claim 1, wherein the promoter is selected from a group consisting of trc promoter, tac promoter, Anderson promoter collection as a constitutive promoter, arabinose operon promoter as an inducible promoter and lactose operon promoter.

4. The vector of claim 1, wherein the region that forms complementary binding with the target gene mRNA is 10 to 100 bp.

5. The vector of claim 1, the target gene mRNA is selected from a group consisting of DsRed2 (red fluorescence protein), luxR (luxR family transcriptional regulator), araC (arabinose operon regulatory protein), kanR (kanamycin resistance gene), tyrR (DNA-binding transcriptional dual regulator, tyrosine-binding), ppc (phosphoenolpyruvate carboxylase), csrA (carbon storage regulator), pgi (glucose-6-phosphate isomerase), gltA (citrate synthase), accA (acetyl-CoA carboxyltransferase, alpha subunit), accB (biotin-carboxyl carrier protein), accC (acetyl-CoA carboxylase), accD (acetyl-CoA carboxyltransferase, beta-subunit), aceE (pyruvate dehydrogenase E1p component), aceF (pyruvate dehydrogenase), ackA (acetate kinase A), adiY (arginine decarboxylase regulator), argB (acetylglutamate kinase), argC (N-acetylglutamylphosphate reductase), argG (argininosuccinate synthase), argH (argininosuccinate lyase), asnC (AsnC transcriptional regulator), crp (CRP transcriptional dual regulator), csiD (a predicted protein induced by carbon starvation), csiR (carbon starvation induced regulator), cytR (cytidine regulator), dcuA (dicarboxylate transporter), deoB (phosphopentomutase), deoC (deoxyribose-phosphate aldolase), deoR (deoxyribonucleoside regulator), fabH (betaketoacyl-ACP synthases 3), fadD (fatty acyl-CoA synthase), fadR (fatty acid metabolism regulator protein), fbp (fructose-1,6-bisphosphatase), fnr (fumarate and nitrate reduction regulatory protein), fruR (fructose operon transcriptional repressor), ftsL (essential cell division protein FtsL), ftsQ (essential cell division protein FtsQ), ftsW (essential cell division protein FtsW), ftsZ (essential cell division protein FtsZ), fur (ferric uptake regulator), gabD (succinate semialdehyde dehydrogenase), gabP (GABA permease), gabT (GABA aminotransferase), gadA (glutamate decarboxylase A subunit), gadB (glutamate decarboxylase B subunit), gadC (GABA APC transporter), glcC (glc operon transcriptional activator), glpK (glycerol kinase), glpR (3-Glycerol-3-phosphate regulon repressor), glpX (fructose 1,6-bisphosphatase II), gltA (citrate synthase), hfld (lysogenization regulator), ihfa (Integration host factor alpha), ihfb (Integration host factor beta), ilvB (acetolactate synthase isozyme 1 large subunit), ilvC (acetohydroxy acid isomeroreductase), ilvD (dihydroxy acid dehydratase), ilvG_1 (acetolactate synthase II, large subunit, N-ter fragment), ilvG_2 (acetolactate synthase II, large subunit, C-ter fragment), ilvH (acetolactate synthase isozyme 3 small subunit), ilvL (ilvGEDA operon leader peptide), ilvM (acetolactate synthase isozyme 2 small subunit), ilvN (acetohydroxybutanoate synthase isozyme 2 small subunit), ilvX (Predicted small protein), lexA (transcription regulator LexA), lpxC (UDP-3-O-acyl-N-acetylglucosamine deacetylase), marA (multiple antibiotic resistance protein MarA), metJ (MetJ transcriptional repressor), modE (transcriptional regulator ModE), nadB (L-aspartate oxidase), narL (nitrate/nitrite response regulator), pck (phosphoenolpyruvate carboxykinase), PdhR (pyruvate dehydrogenase complex regulator), phoP (Transcriptional regulatory protein PhoP), pnuC (PnuC NMN transporter), ppsA (phosphoenolpyruvate synthetase), pta (Phosphate acetyltransferase), purA (adenylosuccinate synthetase), purB (adenylosuccinate lyase), purR (HTH-type transcriptional repressor PurR), puuE (4-aminobutyrate aminotransferase), rbsA (ribose import ATP-binding protein Rbs), rbsB (ribose import ATP-binding protein RbsB), rbsD (ribose pyranose), rbsK (ribokinase), rbsR (ribose operon repressor), rcsB (transcriptional regulatory protein RcsB), rutR (HTH-type transcriptional regulator RutR), serA (D-3-phosphoglycerate dehydrogenase), serC (3-phosphoserine aminotransferase), soxS (regulatory protein SoxS), sroD (SroD small RNA), zwf (glucose 6-phosphate-1-dehydrogenase), asnA (asparagine synthetase A), asnB (asparagine synthetase B), carA (carbamoyl phosphate synthetase A), carB (carbamoyl phosphate synthetase B), ddlB (D-alanine-D-alanine ligase B), deoA (thymidine phosphorylase), deoD (purine nucleoside phosphorylase deoD-type), dpiA (transcriptional regulatory protein DpiA), fis (Fis family transcriptional regulator), gadE (DNA-binding transcriptional activator), gadW (transcriptional regulator GadW), gadX (transcriptional regulator GadX), glpF (glycerol uptake facilitator protein), ilvY (IlvY DNA-binding transcriptional dual regulator), ivbL (ilvB operon leader peptide), lhgO (L-2-hydroxyglutarate oxidase), lpd (Lipoamide dehydrogenase), lrp (Lrp transcriptional dual regulator), metB (O-succinylhomoserine lyase), metL (aspartate kinase), mraY (phospho-N-acetylmuramoyl-pentapeptide transferase), mraZ (transcriptional regulator MraZ), murE (UDP-N-acetylmuramoylalanyl-D-glutamate 2,6-diaminopimelate ligase), murF (D-alanyl-D-alanine-adding enzyme), murG (N-acetylglucosaminyl transferase), nac (nitrogen assimilation regulatory protein), nadA (quinolinate synthase), nsrR (nitrite-sensitive transcriptional repressor), panC (pantothenate synthetase), panD (Aspartate 1-decarboxylase), pgl (6-phosphogluconolactonase), pyrB (aspartate carbamoyltransferase, PyrB subunit), pyrC (dihydroorotase), pyrL (aspartate carbamoyltransferase, PyrI subunit), rob (right origin-binding protein), rpe (ribulose phosphate 3-epimerase), talA (transaldolase A), thrA (homoserine dehydrogenase), thrB (homoserine kinase), thrC (threonine synthase), thrL (thr operon leader peptide), tktA (transketolase I), tktB (transketolase II) and torR (torCAD operon response regulator TorR).

6. The vector of claim 1, wherein length of U tail of the rho independent transcription terminator is 4 to 8.

7. A recombinant microorganism transformed with the vector of claim 1.

8. A method for fine-tuning mRNA expression level of a target gene by introducing the vector of claim 1 into a prokaryote or expressing the vector of claim 1 in a prokaryote.

9. The method of claim 8, wherein the prokaryote is selected from a group consisting of *E. Coli., Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus, Clostridium, Corynebacterium, Streptomyces, Bifidobacterium* and *Cyclobacterium*.

10. A method for screening a target gene for producing a target product, the method comprising:
  (a) fine-tuning an expression level of any one or more genes among genes that are present in a target strain for producing the target product and that participate in a biosynthetic pathway for the target product, according to the method of claim 8; and
  (b) selecting a gene in which expression is regulated as the target gene for production of the target product, when a production yield of the target product is improved by fine-tuning the expression level.

11. A method for improving a target product-producing strain, the method comprising:
  (a) fine-tuning an expression level of any one or more genes among genes that are present in a target strain for producing the target product and that participate in a biosynthetic pathway for the target product, according to the method of claim 8;
  (b) screening a gene in which expression is regulated as a target gene for production of the target product, when a production yield of the target product is improved by fine-tuning the expression level; and
  (c) producing a recombinant strain by introducing the screened gene.

* * * * *

SEQUENCE LISTING

<160> NUMBER OF SEQ ID NOS: 92

<210> SEQ ID NO 1
<211> LENGTH: 32
<212> TYPE: DNA
<213> ORGANISM: Artificial Sequence
<220> FEATURE:
<223> OTHER INFORMATION: p1

<400> SEQUENCE: 1
ggccaattca gctggtaccg ggcccccct cg                          32

<210> SEQ ID NO 2
<211> LENGTH: 31
<212> TYPE: DNA
<213> ORGANISM: Artificial Sequence
<220> FEATURE:
<223> OTHER INFORMATION: p2

<400> SEQUENCE: 2
ggccaattgc cggcgagctc caccgcggtg g                          31

<210> SEQ ID NO 3
<211> LENGTH: 35
<212> TYPE: DNA
<213> ORGANISM: Artificial Sequence
<220> FEATURE:
<223> OTHER INFORMATION: p3

<400> SEQUENCE: 3
ggccttaagc ggccgctaac accgtgcgtg ttgac                      35

<210> SEQ ID NO 4
<211> LENGTH: 33
<212> TYPE: DNA
<213> ORGANISM: Artificial Sequence
<220> FEATURE:
<223> OTHER INFORMATION: p4

<400> SEQUENCE: 4
ccggaattgg atcctataaa cgcagaaagg ccc                                    33

<210> SEQ ID NO 5
<211> LENGTH: 40
<212> TYPE: DNA
<213> ORGANISM: Artificial Sequence
<220> FEATURE:
<223> OTHER INFORMATION: p5

<400> SEQUENCE: 5
ctcgccatat atttgtcttt ctgttgggcc attgcattgc                             40

<210> SEQ ID NO 6
<211> LENGTH: 38
<212> TYPE: DNA
<213> ORGANISM: Artificial Sequence
<220> FEATURE:
<223> OTHER INFORMATION: p6

<400> SEQUENCE: 6
cagtgagaac gtcatgcaac cattatcacc gccagagg                               38

<210> SEQ ID NO 7
<211> LENGTH: 55
<212> TYPE: DNA
<213> ORGANISM: Artificial Sequence
<220> FEATURE:
<223> OTHER INFORMATION: p7

<400> SEQUENCE: 7
gccagcagat tatacctgct ggttttttttt ctcgagccag gcatcaaata aaacg           55

<210> SEQ ID NO 8
<211> LENGTH: 74
<212> TYPE: DNA
<213> ORGANISM: Artificial Sequence
<220> FEATURE:
<223> OTHER INFORMATION: p8

<400> SEQUENCE: 8
gggtgatttt acaccaatag acaaatatat ggcgagcagt gagaacgtca tgcaaccatt       60
atcaccgcca gagg                                                         74

<210> SEQ ID NO 9
<211> LENGTH: 34
<212> TYPE: DNA
<213> ORGANISM: Artificial Sequence
<220> FEATURE:
<223> OTHER INFORMATION: p9

<400> SEQUENCE: 9
ggccttaagg gcccgtggat aaccgtatta ccgc                                   34

<210> SEQ ID NO 10
<211> LENGTH: 33
<212> TYPE: DNA
<213> ORGANISM: Artificial Sequence
<220> FEATURE:
<223> OTHER INFORMATION: p10

<400> SEQUENCE: 10
ccggaattgt cgactataaa cgcagaaagg ccc                                    33

<210> SEQ ID NO 11
<211> LENGTH: 27
<212> TYPE: DNA
<213> ORGANISM: Artificial Sequence
<220> FEATURE:
<223> OTHER INFORMATION: p11

<400> SEQUENCE: 11
tattggtgta aaatcacccg ccagcag                                           27

<210> SEQ ID NO 12
<211> LENGTH: 23
<212> TYPE: DNA
<213> ORGANISM: Artificial Sequence
<220> FEATURE:
<223> OTHER INFORMATION: p12

<400> SEQUENCE: 12
gcaaccatta tcaccgccag agg                                               23

<210> SEQ ID NO 13
<211> LENGTH: 40
<212> TYPE: DNA
<213> ORGANISM: Artificial Sequence
<220> FEATURE:
<223> OTHER INFORMATION: J23100-f

<400> SEQUENCE: 13
gactgagcta gccgtcaagc ggccgccacc gcggtggagc                             40

<210> SEQ ID NO 14
<211> LENGTH: 39
<212> TYPE: DNA
<213> ORGANISM: Artificial Sequence
<220> FEATURE:
<223> OTHER INFORMATION: J23100-r

<400> SEQUENCE: 14
ctaggtacag tgctagcgat gacgttctca ctgctcgcc                              39

<210> SEQ ID NO 15
<211> LENGTH: 39
<212> TYPE: DNA
<213> ORGANISM: Artificial Sequence
<220> FEATURE:
<223> OTHER INFORMATION: J23101-f

<400> SEQUENCE: 15
ctaggtatta tgctagcgat gacgttctca ctgctcgcc                              39

<210> SEQ ID NO 16
<211> LENGTH: 40
<212> TYPE: DNA
<213> ORGANISM: Artificial Sequence
<220> FEATURE:
<223> OTHER INFORMATION: J23101-r

<400> SEQUENCE: 16
gactgagcta gctgtaaagc ggccgccacc gcggtggagc                             40

<210> SEQ ID NO 17
<211> LENGTH: 39
<212> TYPE: DNA
<213> ORGANISM: Artificial Sequence
<220> FEATURE:
<223> OTHER INFORMATION: J23102-f

<400> SEQUENCE: 17
ctaggtactg tgctagcgat gacgttctca ctgctcgcc                     39

<210> SEQ ID NO 18
<211> LENGTH: 40
<212> TYPE: DNA
<213> ORGANISM: Artificial Sequence
<220> FEATURE:
<223> OTHER INFORMATION: J23102-r

<400> SEQUENCE: 18
gactgagcta gctgtcaagc ggccgccacc gcggtggagc                    40

<210> SEQ ID NO 19
<211> LENGTH: 39
<212> TYPE: DNA
<213> ORGANISM: Artificial Sequence
<220> FEATURE:
<223> OTHER INFORMATION: J23103-f

<400> SEQUENCE: 19
ctagggatta tgctagcgat gacgttctca ctgctcgcc                     39

<210> SEQ ID NO 20
<211> LENGTH: 40
<212> TYPE: DNA
<213> ORGANISM: Artificial Sequence
<220> FEATURE:
<223> OTHER INFORMATION: J23103-r

<400> SEQUENCE: 20
gactgagcta gctatcaggc ggccgccacc gcggtggagc                    40

<210> SEQ ID NO 21
<211> LENGTH: 39
<212> TYPE: DNA
<213> ORGANISM: Artificial Sequence
<220> FEATURE:
<223> OTHER INFORMATION: J23104-f

<400> SEQUENCE: 21
ctaggtattg tgctagcgat gacgttctca ctgctcgcc                     39

<210> SEQ ID NO 22
<211> LENGTH: 40
<212> TYPE: DNA
<213> ORGANISM: Artificial Sequence
<220> FEATURE:
<223> OTHER INFORMATION: J23104-r

<400> SEQUENCE: 22
gactgagcta gctgtcaagc ggccgccacc gcggtggagc                    40

<210> SEQ ID NO 23
<211> LENGTH: 40
<212> TYPE: DNA
<213> ORGANISM: Artificial Sequence
<220> FEATURE:
<223> OTHER INFORMATION: J23105-f

<400> SEQUENCE: 23
gactgagcta gccgtaaagc ggccgccacc gcggtggagc                                 40

<210> SEQ ID NO 24
<211> LENGTH: 38
<212> TYPE: DNA
<213> ORGANISM: Artificial Sequence
<220> FEATURE:
<223> OTHER INFORMATION: J23105-r

<400> SEQUENCE: 24
ctaggtacta tgctagcgat gacgttctca ctgctcgc                                   38

<210> SEQ ID NO 25
<211> LENGTH: 39
<212> TYPE: DNA
<213> ORGANISM: Artificial Sequence
<220> FEATURE:
<223> OTHER INFORMATION: J23106-f

<400> SEQUENCE: 25
ctaggtatag tgctagcgat gacgttctca ctgctcgcc                                  39

<210> SEQ ID NO 26
<211> LENGTH: 40
<212> TYPE: DNA
<213> ORGANISM: Artificial Sequence
<220> FEATURE:
<223> OTHER INFORMATION: J23106-r

<400> SEQUENCE: 26
gactgagcta gccgtaaagc ggccgccacc gcggtggagc                                 40

<210> SEQ ID NO 27
<211> LENGTH: 39
<212> TYPE: DNA
<213> ORGANISM: Artificial Sequence
<220> FEATURE:
<223> OTHER INFORMATION: J23107-f

<400> SEQUENCE: 27
ctaggtatta tgctagcgat gacgttctca ctgctcgcc                                  39

<210> SEQ ID NO 28
<211> LENGTH: 40
<212> TYPE: DNA
<213> ORGANISM: Artificial Sequence
<220> FEATURE:
<223> OTHER INFORMATION: J23107-r

<400> SEQUENCE: 28
ggctgagcta gccgtaaagc ggccgccacc gcggtggagc                                 40

<210> SEQ ID NO 29
<211> LENGTH: 40
<212> TYPE: DNA
<213> ORGANISM: Artificial Sequence
<220> FEATURE:
<223> OTHER INFORMATION: J23109-f

<400> SEQUENCE: 29
gactgagcta gctgtaaagc ggccgccacc gcggtggagc                                 40

<210> SEQ ID NO 30

<210> SEQ ID NO 30
<211> LENGTH: 38
<212> TYPE: DNA
<213> ORGANISM: Artificial Sequence
<220> FEATURE:
<223> OTHER INFORMATION: J23109-r

<400> SEQUENCE: 30
ctagggactg tgctagcgat gacgttctca ctgctcgc            38

<210> SEQ ID NO 31
<211> LENGTH: 39
<212> TYPE: DNA
<213> ORGANISM: Artificial Sequence
<220> FEATURE:
<223> OTHER INFORMATION: J23111-f

<400> SEQUENCE: 31
ctaggtatag tgctagcgat gacgttctca ctgctcgcc           39

<210> SEQ ID NO 32
<211> LENGTH: 40
<212> TYPE: DNA
<213> ORGANISM: Artificial Sequence
<220> FEATURE:
<223> OTHER INFORMATION: J23111-r

<400> SEQUENCE: 32
gactgagcta gccgtcaagc ggccgccacc gcggtggagc          40

<210> SEQ ID NO 33
<211> LENGTH: 39
<212> TYPE: DNA
<213> ORGANISM: Artificial Sequence
<220> FEATURE:
<223> OTHER INFORMATION: J23112-f

<400> SEQUENCE: 33
ctagggatta tgctagcgat gacgttctca ctgctcgcc           39

<210> SEQ ID NO 34
<211> LENGTH: 40
<212> TYPE: DNA
<213> ORGANISM: Artificial Sequence
<220> FEATURE:
<223> OTHER INFORMATION: J23112-r

<400> SEQUENCE: 34
gactgagcta gctatcaggc ggccgccacc gcggtggagc          40

<210> SEQ ID NO 35
<211> LENGTH: 39
<212> TYPE: DNA
<213> ORGANISM: Artificial Sequence
<220> FEATURE:
<223> OTHER INFORMATION: J23113-f

<400> SEQUENCE: 35
ctagggatta tgctagcgat gacgttctca ctgctcgcc           39

<210> SEQ ID NO 36
<211> LENGTH: 40
<212> TYPE: DNA
<213> ORGANISM: Artificial Sequence
<220> FEATURE:
<223> OTHER INFORMATION: J23113-r

<400> SEQUENCE: 36
gactgagcta gccatcaggc ggccgccacc gcggtggagc					40

<210> SEQ ID NO 37
<211> LENGTH: 40
<212> TYPE: DNA
<213> ORGANISM: Artificial Sequence
<220> FEATURE:
<223> OTHER INFORMATION: J23114-f

<400> SEQUENCE: 37
gactgagcta gccataaagc ggccgccacc gcggtggagc					40

<210> SEQ ID NO 38
<211> LENGTH: 38
<212> TYPE: DNA
<213> ORGANISM: Artificial Sequence
<220> FEATURE:
<223> OTHER INFORMATION: J23114-r

<400> SEQUENCE: 38
ctaggtacaa tgctagcgat gacgttctca ctgctcgc					38

<210> SEQ ID NO 39
<211> LENGTH: 39
<212> TYPE: DNA
<213> ORGANISM: Artificial Sequence
<220> FEATURE:
<223> OTHER INFORMATION: J23115-f

<400> SEQUENCE: 39
cttggtacaa tgctagcgat gacgttctca ctgctcgcc					39

<210> SEQ ID NO 40
<211> LENGTH: 40
<212> TYPE: DNA
<213> ORGANISM: Artificial Sequence
<220> FEATURE:
<223> OTHER INFORMATION: J23115-r

<400> SEQUENCE: 40
ggctgagcta gctataaagc ggccgccacc gcggtggagc					40

<210> SEQ ID NO 41
<211> LENGTH: 39
<212> TYPE: DNA
<213> ORGANISM: Artificial Sequence
<220> FEATURE:
<223> OTHER INFORMATION: J23116-f

<400> SEQUENCE: 41
ctagggacta tgctagcgat gacgttctca ctgctcgcc					39

<210> SEQ ID NO 42
<211> LENGTH: 40
<212> TYPE: DNA
<213> ORGANISM: Artificial Sequence
<220> FEATURE:
<223> OTHER INFORMATION: J23116-r

<400> SEQUENCE: 42
gactgagcta gctgtcaagc ggccgccacc gcggtggagc					40

<210> SEQ ID NO 43
<211> LENGTH: 39
<212> TYPE: DNA

```
<213> ORGANISM: Artificial Sequence
<220> FEATURE:
<223> OTHER INFORMATION: J23117-f

<400> SEQUENCE: 43
ctagggattg tgctagcgat gacgttctca ctgctcgcc                    39

<210> SEQ ID NO 44
<211> LENGTH: 40
<212> TYPE: DNA
<213> ORGANISM: Artificial Sequence
<220> FEATURE:
<223> OTHER INFORMATION: J23117-r

<400> SEQUENCE: 44
gactgagcta gctgtcaagc ggccgccacc gcggtggagc                   40

<210> SEQ ID NO 45
<211> LENGTH: 39
<212> TYPE: DNA
<213> ORGANISM: Artificial Sequence
<220> FEATURE:
<223> OTHER INFORMATION: J23118-f

<400> SEQUENCE: 45
ctaggtattg tgctagcgat gacgttctca ctgctcgcc                    39

<210> SEQ ID NO 46
<211> LENGTH: 40
<212> TYPE: DNA
<213> ORGANISM: Artificial Sequence
<220> FEATURE:
<223> OTHER INFORMATION: J23118-r

<400> SEQUENCE: 46
gactgagcta gccgtcaagc ggccgccacc gcggtggagc                   40

<210> SEQ ID NO 47
<211> LENGTH: 30
<212> TYPE: DNA
<213> ORGANISM: Artificial Sequence
<220> FEATURE:
<223> OTHER INFORMATION: p47

<400> SEQUENCE: 47
aatcacccgc cagcagatta tacctgctgg                              30

<210> SEQ ID NO 48
<211> LENGTH: 29
<212> TYPE: DNA
<213> ORGANISM: Artificial Sequence
<220> FEATURE:
<223> OTHER INFORMATION: p48

<400> SEQUENCE: 48
ttagtccaat aatggcgagc agtgagaac                               29

<210> SEQ ID NO 49
<211> LENGTH: 29
<212> TYPE: DNA
<213> ORGANISM: Artificial Sequence
<220> FEATURE:
<223> OTHER INFORMATION: p49

<400> SEQUENCE: 49
ttacaggaat aatggcgagc agtgagaac                               29
```

<210> SEQ ID NO 50
<211> LENGTH: 29
<212> TYPE: DNA
<213> ORGANISM: Artificial Sequence
<220> FEATURE:
<223> OTHER INFORMATION: p50

<400> SEQUENCE: 50
ttagtggaat aatggcgagc agtgagaac                     29

<210> SEQ ID NO 51
<211> LENGTH: 40
<212> TYPE: DNA
<213> ORGANISM: Artificial Sequence
<220> FEATURE:
<223> OTHER INFORMATION: J23108-f

<400> SEQUENCE: 51
gactgagcta gctgtcaggc ggccgccacc gcggtggagc         40

<210> SEQ ID NO 52
<211> LENGTH: 39
<212> TYPE: DNA
<213> ORGANISM: Artificial Sequence
<220> FEATURE:
<223> OTHER INFORMATION: J23108-r

<400> SEQUENCE: 52
ctaggtataa tgctagcgat gacgttctca ctgctcgcc          39

<210> SEQ ID NO 53
<211> LENGTH: 31
<212> TYPE: DNA
<213> ORGANISM: Artificial Sequence
<220> FEATURE:
<223> OTHER INFORMATION: 6nt-53

<400> SEQUENCE: 53
ttacccacca ataatggcga gcagtgagaa c                  31

<210> SEQ ID NO 54
<211> LENGTH: 32
<212> TYPE: DNA
<213> ORGANISM: Artificial Sequence
<220> FEATURE:
<223> OTHER INFORMATION: 6nt-54

<400> SEQUENCE: 54
aatcccaccc gccagcagat tatacctgct gg                 32

<210> SEQ ID NO 55
<211> LENGTH: 33
<212> TYPE: DNA
<213> ORGANISM: Artificial Sequence
<220> FEATURE:
<223> OTHER INFORMATION: 8nt-55

<400> SEQUENCE: 55 ttaccccac caataatggc gagcagtgag aac                 33

<210> SEQ ID NO 56
<211> LENGTH: 34
<212> TYPE: DNA
<213> ORGANISM: Artificial Sequence
<220> FEATURE:

<223> OTHER INFORMATION: 8nt-56

<400> SEQUENCE: 56
aatcccccac ccgccagcag attatacctg ctgg         34

<210> SEQ ID NO 57
<211> LENGTH: 20
<212> TYPE: DNA
<213> ORGANISM: Artificial Sequence
<220> FEATURE:
<223> OTHER INFORMATION: 57

<400> SEQUENCE: 57
ggacaccaat aatggcgagc         20

<210> SEQ ID NO 58
<211> LENGTH: 23
<212> TYPE: DNA
<213> ORGANISM: Artificial Sequence
<220> FEATURE:
<223> OTHER INFORMATION: p58

<400> SEQUENCE: 58
ggtcacccgc cagcagatta tac         23

<210> SEQ ID NO 59
<211> LENGTH: 20
<212> TYPE: DNA
<213> ORGANISM: Artificial Sequence
<220> FEATURE:
<223> OTHER INFORMATION: p59

<400> SEQUENCE: 59
ggacaccaat aatggcgagc         20

<210> SEQ ID NO 60
<211> LENGTH: 23
<212> TYPE: DNA
<213> ORGANISM: Artificial Sequence
<220> FEATURE:
<223> OTHER INFORMATION: p60

<400> SEQUENCE: 60
cctcacccgc cagcagatta tac         23

<210> SEQ ID NO 61
<211> LENGTH: 20
<212> TYPE: DNA
<213> ORGANISM: Artificial Sequence
<220> FEATURE:
<223> OTHER INFORMATION: p61

<400> SEQUENCE: 61
ggacaccaat aatggcgagc         20

<210> SEQ ID NO 62
<211> LENGTH: 23
<212> TYPE: DNA
<213> ORGANISM: Artificial Sequence
<220> FEATURE:
<223> OTHER INFORMATION: p62

<400> SEQUENCE: 62
tttcacccgc cagcagatta tac         23

```
<210> SEQ ID NO 63
<211> LENGTH: 20
<212> TYPE: DNA
<213> ORGANISM: Artificial Sequence
<220> FEATURE:
<223> OTHER INFORMATION: p63

<400> SEQUENCE: 63
ccacaccaat aatggcgagc                                              20

<210> SEQ ID NO 64
<211> LENGTH: 23
<212> TYPE: DNA
<213> ORGANISM: Artificial Sequence
<220> FEATURE:
<223> OTHER INFORMATION: p64

<400> SEQUENCE: 64
ggtcacccgc cagcagatta tac                                          23

<210> SEQ ID NO 65
<211> LENGTH: 20
<212> TYPE: DNA
<213> ORGANISM: Artificial Sequence
<220> FEATURE:
<223> OTHER INFORMATION: p65

<400> SEQUENCE: 65
ccacaccaat aatggcgagc                                              20

<210> SEQ ID NO 66
<211> LENGTH: 23
<212> TYPE: DNA
<213> ORGANISM: Artificial Sequence
<220> FEATURE:
<223> OTHER INFORMATION: p66

<400> SEQUENCE: 66
cctcacccgc cagcagatta tac                                          23

<210> SEQ ID NO 67
<211> LENGTH: 20
<212> TYPE: DNA
<213> ORGANISM: Artificial Sequence
<220> FEATURE:
<223> OTHER INFORMATION: p67

<400> SEQUENCE: 67
ccacaccaat aatggcgagc                                              20

<210> SEQ ID NO 68
<211> LENGTH: 23
<212> TYPE: DNA
<213> ORGANISM: Artificial Sequence
<220> FEATURE:
<223> OTHER INFORMATION: p68

<400> SEQUENCE: 68
tttcacccgc cagcagatta tac                                          23

<210> SEQ ID NO 69
<211> LENGTH: 20
<212> TYPE: DNA
<213> ORGANISM: Artificial Sequence
<220> FEATURE:
<223> OTHER INFORMATION: p69
```

<400> SEQUENCE: 69
aaacaccaat aatggcgagc                                               20

<210> SEQ ID NO 70
<211> LENGTH: 23
<212> TYPE: DNA
<213> ORGANISM: Artificial Sequence
<220> FEATURE:
<223> OTHER INFORMATION: p70

<400> SEQUENCE: 70
ggtcacccgc cagcagatta tac                                           23

<210> SEQ ID NO 71
<211> LENGTH: 20
<212> TYPE: DNA
<213> ORGANISM: Artificial Sequence
<220> FEATURE:
<223> OTHER INFORMATION: p71

<400> SEQUENCE: 71
aaacaccaat aatggcgagc                                               20

<210> SEQ ID NO 72
<211> LENGTH: 23
<212> TYPE: DNA
<213> ORGANISM: Artificial Sequence
<220> FEATURE:
<223> OTHER INFORMATION: p72

<400> SEQUENCE: 72
cctcacccgc cagcagatta tac                                           23

<210> SEQ ID NO 73
<211> LENGTH: 20
<212> TYPE: DNA
<213> ORGANISM: Artificial Sequence
<220> FEATURE:
<223> OTHER INFORMATION: p73

<400> SEQUENCE: 73
aaacaccaat aatggcgagc                                               20

<210> SEQ ID NO 74
<211> LENGTH: 23
<212> TYPE: DNA
<213> ORGANISM: Artificial Sequence
<220> FEATURE:
<223> OTHER INFORMATION: p74

<400> SEQUENCE: 74
tttcacccgc cagcagatta tac                                           23

<210> SEQ ID NO 75
<211> LENGTH: 20
<212> TYPE: DNA
<213> ORGANISM: Artificial Sequence
<220> FEATURE:
<223> OTHER INFORMATION: p75

<400> SEQUENCE: 75
gacaaatata tggcgagcag                                               20

<210> SEQ ID NO 76
<211> LENGTH: 27

```
<212> TYPE: DNA
<213> ORGANISM: Artificial Sequence
<220> FEATURE:
<223> OTHER INFORMATION: p76

<400> SEQUENCE: 76
gattggtgta aaatcacccg ccagcag                                            27

<210> SEQ ID NO 77
<211> LENGTH: 28
<212> TYPE: DNA
<213> ORGANISM: Artificial Sequence
<220> FEATURE:
<223> OTHER INFORMATION: p77

<400> SEQUENCE: 77
gtcttggtgt aaaatcaccc gccagcag                                           28

<210> SEQ ID NO 78
<211> LENGTH: 27
<212> TYPE: DNA
<213> ORGANISM: Artificial Sequence
<220> FEATURE:
<223> OTHER INFORMATION: p78

<400> SEQUENCE: 78
tactggtgta aaatcacccg ccagcag                                            27

<210> SEQ ID NO 79
<211> LENGTH: 27
<212> TYPE: DNA
<213> ORGANISM: Artificial Sequence
<220> FEATURE:
<223> OTHER INFORMATION: p79

<400> SEQUENCE: 79
taatggtgta aaatcacccg ccagcag                                            27

<210> SEQ ID NO 80
<211> LENGTH: 27
<212> TYPE: DNA
<213> ORGANISM: Artificial Sequence
<220> FEATURE:
<223> OTHER INFORMATION: p80

<400> SEQUENCE: 80
tatcggtgta aaatcacccg ccagcag                                            27

<210> SEQ ID NO 81
<211> LENGTH: 27
<212> TYPE: DNA
<213> ORGANISM: Artificial Sequence
<220> FEATURE:
<223> OTHER INFORMATION: p81

<400> SEQUENCE: 81
tataggtgta aaatcacccg ccagcag                                            27

<210> SEQ ID NO 82
<211> LENGTH: 27
<212> TYPE: DNA
<213> ORGANISM: Artificial Sequence
<220> FEATURE:
<223> OTHER INFORMATION: p82

<400> SEQUENCE: 82
```

```
gcccggtgta aaatcacccg ccagcag                                              27

<210> SEQ ID NO 83
<211> LENGTH: 27
<212> TYPE: DNA
<213> ORGANISM: Artificial Sequence
<220> FEATURE:
<223> OTHER INFORMATION: p83

<400> SEQUENCE: 83
gcacggtgta aaatcacccg ccagcag                                              27

<210> SEQ ID NO 84
<211> LENGTH: 27
<212> TYPE: DNA
<213> ORGANISM: Artificial Sequence
<220> FEATURE:
<223> OTHER INFORMATION: p84

<400> SEQUENCE: 84
gaccggtgta aaatcacccg ccagcag                                              27

<210> SEQ ID NO 85
<211> LENGTH: 27
<212> TYPE: DNA
<213> ORGANISM: Artificial Sequence
<220> FEATURE:
<223> OTHER INFORMATION: p85

<400> SEQUENCE: 85
gaccggtgta aaatcacccg ccagcag                                              27

<210> SEQ ID NO 86
<211> LENGTH: 12
<212> TYPE: DNA
<213> ORGANISM: Artificial Sequence
<220> FEATURE:
<223> OTHER INFORMATION: p86

<400> SEQUENCE: 86
ctcgagccag gc                                                              12

<210> SEQ ID NO 87
<211> LENGTH: 30
<212> TYPE: DNA
<213> ORGANISM: Artificial Sequence
<220> FEATURE:
<223> OTHER INFORMATION: u7-87

<400> SEQUENCE: 87
aaaaaaacca gcaggtataa tctgctggcg                                           30

<210> SEQ ID NO 88
<211> LENGTH: 29
<212> TYPE: DNA
<213> ORGANISM: Artificial Sequence
<220> FEATURE:
<223> OTHER INFORMATION: u6-88

<400> SEQUENCE: 88
aaaaaaccag caggtataat ctgctggcg                                            29

<210> SEQ ID NO 89
<211> LENGTH: 28
<212> TYPE: DNA
<213> ORGANISM: Artificial Sequence
```

```
<220> FEATURE:
<223> OTHER INFORMATION: u5-89

<400> SEQUENCE: 89
aaaaaccagc aggtataatc tgctggcg                                          28

<210> SEQ ID NO 90
<211> LENGTH: 27
<212> TYPE: DNA
<213> ORGANISM: Artificial Sequence
<220> FEATURE:
<223> OTHER INFORMATION: u4-90

<400> SEQUENCE: 90
aaaaccagca ggtataatct gctggcg                                           27

<210> SEQ ID NO 91
<211> LENGTH: 49
<212> TYPE: RNA
<213> ORGANISM: Artificial Sequence
<220> FEATURE:
<223> OTHER INFORMATION: SgrS-sRNA

<400> SEQUENCE: 91
uauuggugua aaaucacccg ccagcagauu auaccugcug guuuuuuuu                   49

<210> SEQ ID NO 92
<211> LENGTH: 60
<212> TYPE: RNA
<213> ORGANISM: Artificial Sequence
<220> FEATURE:
<223> OTHER INFORMATION: SgrS-sRNA
<220> FEATURE:
<221> NAME/KEY: misc_feature
<222> LOCATION: (1)..(11)
<223> OTHER INFORMATION: n =  a, c, g, or u

<400> SEQUENCE: 92 nnnnnnnnnnn nuauuggugu aaaucaccc gccagcagau uauaccugcu gguuuuuuuu       60
```

UNITED STATES PATENT AND TRADEMARK OFFICE
CERTIFICATE OF CORRECTION

PATENT NO. : 10,196,644 B2  
APPLICATION NO. : 15/317939  
DATED : February 5, 2019  
INVENTOR(S) : Sang Yup Lee Page 1 of 1

It is certified that error appears in the above-identified patent and that said Letters Patent is hereby corrected as shown below:

In the Specification

Column 9, Line 24: "DH5a" should be -- DH5α --.

Column 10, Line 14: "DH5a" should be -- DH5α --.

Column 10, Line 33: "DH5a" should be -- DH5α --.

Signed and Sealed this  
Twenty-sixth Day of March, 2019

Andrei Iancu  
*Director of the United States Patent and Trademark Office*